(12) United States Patent
Imai et al.

(10) Patent No.: US 8,173,400 B2
(45) Date of Patent: May 8, 2012

(54) METHOD OF DETECTING OR QUANTITATING ENDOGENOUS WHEAT DNA AND METHOD OF DETERMINING CONTAMINATION RATE OF GENETICALLY MODIFIED WHEAT IN TEST SAMPLE

(75) Inventors: Shinjiro Imai, Fujimino (JP); Keiko Tanaka, Fujimino (JP)

(73) Assignee: Nisshin Seifun Group Inc., Tokyo (JP)

( * ) Notice: Subject to any disclaimer, the term of this patent is extended or adjusted under 35 U.S.C. 154(b) by 219 days.

(21) Appl. No.: 12/300,973

(22) PCT Filed: May 11, 2007

(86) PCT No.: PCT/JP2007/059727
§ 371 (c)(1),
(2), (4) Date: Nov. 14, 2008

(87) PCT Pub. No.: WO2007/132760
PCT Pub. Date: Nov. 22, 2007

(65) Prior Publication Data
US 2010/0062432 A1    Mar. 11, 2010

(30) Foreign Application Priority Data
May 15, 2006    (JP) ................................. 2006-135835

(51) Int. Cl.
C12P 19/34        (2006.01)
C12Q 1/68         (2006.01)
(52) U.S. Cl. ........................................ 435/91.2; 435/6.1
(58) Field of Classification Search .................. 435/91.2, 435/91.21
See application file for complete search history.

(56) References Cited

U.S. PATENT DOCUMENTS
8,030,463 B2   10/2011  Hino et al.
2009/0011411 A1   1/2009  Hino et al.

FOREIGN PATENT DOCUMENTS
| EP | 1 482 058 A1 | 12/2004 |
| EP | 1 736 543 | 12/2006 |
| JP | 6-125669 | 5/1994 |
| JP | 7-501682 | 2/1995 |
| JP | 2003-284598 | 10/2003 |
| WO | WO 91/13991 | 9/1991 |
| WO | WO 98/04737 | 2/1998 |
| WO | WO 03/068989 | 8/2003 |
| WO | WO 2005/097989 | 10/2005 |

OTHER PUBLICATIONS

Lowes et al., Nucleic acids research, vol. 18, No. 7, pp. 1757-1761, 1990.*
International Search Report and Written Opinion for International Application No. PCT/JP2007/059727, (Jan. 15, 2009).
"Manual of Assessment and Analysis for Genetically Modified Foods," Revised Second Edition; JAS Analytical Test Handbook, Jun. 18, 2003.

"Concerning Test Methods for Foods Modified by Recombinant DNA Technology (Partially Revised)", Notice No. 0618001 of the Food Sanitation Department, Ministry of Health, Labor and Welfare, Jun. 18, 2003.
"Concerning Test Methods for Foods Modified by Recombinant DNA Technology (Partially Revised)," Notice No. 1113001 of the Food Sanitation Department, Ministry of Health, Labor and Welfare, Nov. 13, 2003.
Aoki, Naohiro, et al.; "Three Sucrose Transporter Genes Are Expressed in the Developing Grain of Hexaploid Wheat;" Plant Molecular Biology 50: 2002; pp. 453-462.
Waiblinger, H.U., et al.; "A Screening Method for the Identification of Genetically Modified Food of Plant Origin;" Foods Produced by Means of Genetic Engineering, $2^{nd}$ Status Report, Jan. 1997; pp. 118-122.
Koppel, E., et al.; "Sensitive Method for the Detection of the Genetically Engineered Soy Bean 'Roundup Ready'"; Mitt. Gebiete Lebensm, Hyg. 88; 1997; pp. 164-175, Summary only.
Murai, J. et al.; "Isolation and Characterization of the Three Waxy Genes Encoding the Granule-Bound Starch Synthase in Hexaploid Wheat," Gene, 234; Japan, May 3, 1999; pp. 71-79.
Ainsworth, Charles, et al.; "Expression, Organisation and Structure of the Genes Encoding the Waxy Protein (Granule-Bound Starch Synthase) in Wheat;" Plant Molecular Biology 22; 1993; pp. 67-82.
Raines, C.A., et al., "A Novel Proline-Rich Protein From Wheat," Plant Molecular Biology 16; 1991; and Abstract, retrieved on Jun. 1, 2007 from www.ncbi.nlm.nih.gov/pubmed/1714320? dopt= Abstract Plus; Apr. 1991, pp. 663-670.
Raines, C.A. et al.; "*T. aestivum* mRNA for a proline-rich protein;" retrieved on Sep. 12, 1993 from www.ncbi.nlm.nih.gov/entrez/viewer.fcgi?db=nucleotideval=21841.
European Search Report dated Apr. 17, 2009 for Application No. 05728798.9-2403.
Allmann, Michael, et al., Polymerase chain reaction (PCR): a possible alternative to immunochemical methods assuring safety and quality of food, Z Lebensm Unters Forsch (1993) 196:248-251.

(Continued)

*Primary Examiner* — Gary Benzion
*Assistant Examiner* — Cynthia Wilder
(74) *Attorney, Agent, or Firm* — Finnegan, Henderson, Farabow, Garrett & Dunner, L.L.P.

(57) ABSTRACT

An object of the present invention is to discover an endogenous wheat sequence satisfying the conditions of: a) it is universally present in varieties of wheat, b) the amount present (detected amount) is not affected by the wheat variety, c) even if other grains are present, only wheat can be detected without cross-reactivity, and d) it is amplified quantitatively by the PCR reaction. A further object of the present invention is to provide a method of accurately detecting and quantitating endogenous wheat DNA in a test sample by the polymerase chain reaction. The present invention provides a method of detecting or quantitating endogenous wheat DNA in a test sample by the polymerase chain reaction, the method comprising: a step of using a nucleic acid molecule in the test sample or a nucleic acid molecule extracted from the test sample as a template to amplify the nucleic acid molecule of a region consisting of the nucleotide sequence identified as SEQ ID NO: 2 or a partial sequence thereof with a primer pair capable of amplifying that region; and a step of detecting or quantitating the amplified nucleic acid molecule.

10 Claims, 7 Drawing Sheets

OTHER PUBLICATIONS

Hübner, Philipp, et al., Validation of PCR Methods for Quantitation of Genetically Modified Plants in Food, Journal of AOAC International (2001) 84(6):1855-1864.

Iida, Mayu, et al., Development of Taxon-Specific Sequences of Common Wheat for the Detection of Genetically Modified Wheat, Journal of Agricultural and Food Chemistry (2005) 53:6294-6300.

Studer, Edgar, et al., Quantitative Competitive PCR for the Detection of Genetically Modified Soybean and Maize, Z Lebensm Unters Forsch A (1998) 207:207-213.

Terzi, Valeria, et al., Development of Analytical Systems based on Real-Time PCR for *Triticum* Species-Specific Detection and Quantitation of Bread Wheat Contamination in Semolina and Pasta, Journal of Cereal Science (2003) 38:87-94.

Yamakawa, Hirohito, et al., Specific Detection of Wheat Residues in Processed Foods by Polymerase Chain Reaction, Bioscience, Biotechnology, and Biochemistry (2007) 71(10): 2561-2564.

Aoki et al., "Three Sucrose Transporter Genes are Expressed in the Developing Grain of Hexaploid Wheat," *Plant Molecular Biology*, (2002) pp. 453-462 vol. 50 No. 3.

European Search Report in corresponding application No. 09015932.8 dated Mar. 24, 2010.

European Search Report in corresponding application No. 09015931.0 dated Mar. 24, 2010.

European Search Report in corresponding EP Application No. EP 07743162.5, dated Jun. 10, 2010.

Feuillet et al., "Genetic and Physical Characterization of the LR1 Leaf Rust Resistance Locus in Wheat (Triticum Aestivum L.)," *Molecular and General Genetics*, (1995) pp. 553-562 vol. 248 No. 5.

JAS Analytical Handbook, Manual of Assessment and Analysis for Genetically Modified Foods; Revised Second Edition, 67 pages, (Jun. 20, 2002).

Ling et al., "High-Resolution Mapping of the Leaf Rust Disease Resistance Gene Lr1 in Wheat and Characterization of BAC Clones From the Lr1 Locus," *Theoretical and Applied Genetics*, (2003) pp. 875-882 vol. 106 No. 5.

McNeil et al., "Amplification of DNA sequences in wheat and its relatives: the Dgas44 and R350 families of repetitive sequences," *Genome*, 37(2):320-327 (1994).

Nakamura et al., "Rapid classification of partial waxy wheats using PCR-based markers," *Genome*, 45(6): 1150-1156 (2002).

Database record for GenBank Accession No. AF113844, *Triticum aestivum granule-bound starch synthase precursor (Wx-D1) mRNA, Wx-D1b allele, complete cds* (Apr. 20, 1999).

Database record for GenBank Accession No. AF408845, *Triticum aestivum sucrose transporter SUT1D gene, complete cd* (Mar. 19, 2002).

Database record for GenBank Accession No. AJ440705, *Triticum aestivum GSS clone PSR1205 forward sequence, genomic survey sequence* (Jul. 31, 2003).

Database record for GenBank Accession No. J02817, *Wheat gibberellin responsive protein gene, complete cds* (Apr. 27, 1993).

Database record for GenBank Accession No. S79982, *Lr1 (TLR621)=leaf rust resistance gene [Triticum aestivum=wheat, Genomic, 915 nt]* (Feb. 12, 1997).

Database record for GenBank Accession No. S79983, *Lr1 (TH621)=leaf rust resistance gene [Triticum aestivum=wheat, Genomic, 892 nt]* (Feb. 12, 1997).

Office Action mailed Jul. 7, 2010, in U.S. Appl. No. 11/578,107.

Yan et al., "Sequences of the *Waxy*Loci of Wheat: Utility in Analysis of Waxy Proteins and Developing Molecular Markers," Biochemical Genetics, 38(11/12): 391-411 (2000).

Reply to Office Action filed Oct. 5, 2010, in U.S. Appl. No. 11/578,107.

Final Office Action mailed Jan. 11, 2011, in U.S. Appl. No. 11/578,107.

Amendment under 37 C.F.R. § 1.1116 filed Apr. 26, 2011, in U.S. Appl. No. 11/578,107.

Notice of Allowance and Fee(s) Due mailed Apr. 28, 2011, in U.S. Appl. No. 11/578,107.

Notice of Allowance and Fee(s) Due mailed May 31, 2011, in U.S. Appl. No. 11/578,107.

\* cited by examiner (A)

(B)

(C)

METHOD OF DETECTING OR QUANTITATING ENDOGENOUS WHEAT DNA AND METHOD OF DETERMINING CONTAMINATION RATE OF GENETICALLY MODIFIED WHEAT IN TEST SAMPLE

CROSS REFERENCE TO RELATED APPLICATIONS

This application is a national phase application of International Application Number PCT/JP2007/059727, filed May 11, 2007, and claims the priority of Japanese Patent Application No. 2006-135835, filed May 15, 2006, the contents of both of which are incorporated herein by reference.

BACKGROUND

The present invention relates to a method of detecting or quantitating endogenous wheat DNA in a test sample, and more particularly to a method of detecting or quantitating endogenous wheat DNA to be used when determining the contamination rate of genetically modified wheat contained in a food material or processed food.

In Japan more than 50 varieties of genetically modified crops (hereinafter, "genetically modified organism" or "GMO") including maize, soybeans, and potatoes have undergone a safety assessment and have been approved for import and sale. Accordingly, a food product containing a GMO must be labeled based on the "Labeling Standard for Genetically Modified Foods issued by the Ministry of Agriculture, Forestry and Fisheries that was established in accordance with Article 7, paragraph 1 of the Quality Labeling Standard for Processed Foods and on Article 7, paragraph 1 of the Quality Labeling Standard for Fresh Foods" (Notification No. 517 of the Ministry of Agriculture, Forestry and Fisheries, 31 Mar. 2000), and on the "Enforcement of Ministerial Ordinance amending portions of Ministerial Ordinances on the Food Sanitation Law Enforcement Regulations and Concerning Compositional Standards, etc. for Milk and Milk Products" (Notice No. 79 of the Food Sanitation Department, Pharmaceutical and Medical Safety Bureau, Ministry of Health, Labor and Welfare 15 Mar. 2001).

In foreign countries, however, GMO crops may sometimes be cultivated together with non-GMO crops once the safety evaluation has been completed, and contamination may occur after harvest during the distribution process. The makers of food products and the like often subcontract the manufacturing of processed foods to manufacturing plants, and even though the contract may stipulate to use a non-GMO material, small amounts of a GMO may contaminate processed foods if a GMO is also used in the same plant. Therefore, to comply with the labeling obligations the makers of food products must inspect and analyze the finished processed food products to verify that they are not contaminated with a GMO.

Test methods for detecting a GMO in a test sample of a processed food, the raw material thereof, etc., include the detection of recombinant DNA by the polymerase chain reaction (hereinafter, "PCR") and the detection of a recombinant protein by ELISA. In the case of processed foods, however, proteins often become denatured by heat and pressure, and they cannot be detected accurately by ELISA. Therefore, detection by PCR is commonly used.

Methods of laboratory analysis include the methods described in JAS Analytical Test Handbook, "Genetically Modified Food Test and Analysis Manual for Individual Products, Revised Second Edition (Non-Patent Document 1)" and those described in "Testing for Foods Produced by Recombinant DNA Techniques (Partially Revised)" (Notice No. 0618002 of the Food Sanitation Department, Ministry of Health, Labor and Welfare, Jun. 18, 2003). These documents describe that in the testing and analysis of a GMO it is necessary to perform PCR using a primer pair recognizing the endogenous DNA of each agricultural product and to verify that a PCR product of the predicted length is obtained for verification that DNA extracted from the test sample can be amplified by PCR. When quantitating a GMO contained in a test sample, a method is used of measuring the contamination rate of the modified crop based on the ratio of recombinant DNA to endogenous DNA that is always present in that crop.

In the case of maize for example, primer pairs have been developed that recognize each of the 5 strains of approved GMO varieties, along with a primer pair that recognizes the SSIIB gene region as an endogenous maize DNA (Non-patent document 1).

In "Testing for Foods Produced by Recombinant DNA Techniques (Partially Revised)" (Notice No. 1113001 of the Food Sanitation Department, Ministry of Health, Labor and Welfare, 13 Nov. 2003), during the process of performing quantitative PCR, the amplification products amplified by specific primer pairs targeting endogenous DNA and recombinant DNA of maize or soybean are ligated to a plasmid and used as a standard reference material. By performing PCR using this standard reference material, the ratio of the number of copies of recombinant DNA to the number of copies of endogenous DNA can be accurately determined in a test sample by fixed-time, quantitative PCR.

When there are a plurality of GMO strains, as in the case of maize, one particularly useful technique is to utilize a common standard reference material to measure the contamination rate of each strain, which can be done by using a standard reference material having endogenous DNA and DNAs specific to each strain incorporated into a single circular DNA molecule.

It is generally difficult to obtain genes specific to each strain, but once replicable DNA incorporating those genes has been prepared, it is possible to stably provide strain-specific DNA by replication thereof.

While no genetically modified products of common wheat have yet passed safety assessment, they are expected to appear on the market in the near future. Consequently, methods for detecting and quantitating endogenous wheat DNA and PCR primer pairs for use in such methods need to be developed to prepare for the distribution of GMO wheat.

The forms of genes found in wheat have diverse variations compared with other grains. That is because hexaploid, tetraploid, and diploid genotypes occur depending on the variety of wheat. For example, general common wheat is hexaploid (AA, BB, DD), and although each of the genes is similar, partial differences are found due to translocation and the like. On the other hand, durum wheat is tetraploid and does not contain genomic DD.

In terms of its genome structure and the nucleotide sequence of its encoded genes, wheat shares a high degree of homology with other cereal grains such as barley, rye and oats. These grains have a high level of homology with common wheat, and therefore the possibility of false detection is high.

Under these circumstances, it has been difficult in wheat to discover a DNA sequence satisfying the following four conditions: a) it is universally present in wheat varieties, b) the amount present (detected amount) will not be affected depending on the wheat variety, c) even if other grains are present, only wheat will be detected without cross-reactivity, and d) it will be amplified quantitatively by the PCR reaction.

WO 2005/097989 (Patent Document 1) discloses that a partial sequence of the Waxy gene (see Non-Patent Document 2), etc., can be used as endogenous wheat DNA satisfying such conditions.

Patent Document 1: WO 2005/097989

Non-Patent Document 1: JAS Analytical Test Handbook, "Genetically Modified Food Test and Analysis Manual for Individual Products, Revised Second Edition"

Non-Patent Document 2: Ainsworth C, et al., Plant Mol Biol. 1993 April; 22(1):67-82

DISCLOSURE OF INVENTION

However, waxy wheat, a mutant lacking the Waxy gene, is already known, and in test samples containing waxy wheat it is impossible to assay the endogenous wheat DNA accurately by detecting the partial sequence of the Waxy gene disclosed in Patent Document 1. In addition, since Waxy gene is thought to be present in the D genome of wheat, it will not be present in the genome of durum wheat, which lacks the D genome. Therefore, although the method disclosed in patent document 1 is useful when the goal is to distinguish between durum wheat and common wheat, there are many cases requiring the detection of a total of durum wheat and common wheat as the detection of "wheat," and under those circumstances an endogenous durum wheat DNA sequence must be discovered, detected and quantitated separately.

Therefore, an object of the present invention is to discover an additional endogenous wheat sequence satisfying conditions a) to d) above, and a further object of the present invention is to provide a method of accurately detecting or quantitating endogenous wheat DNA in a test sample by the polymerase chain reaction.

The inventors conducted diligent research to solve the above problem and discovered that a partial region of the proline rich protein (PRP) gene (C. A. Raines, et al., Plant Molecular Biology, 16: 663-670, 1991) in the genomic DNA of wheat is universally present throughout wheat varieties and does not cross-react with other plants in PCR reactions, and that it is possible to specifically detect and quantitate an endogenous wheat DNA sequence by amplifying that region, thus completed the present invention.

More specifically, the present invention relates to:

(1) A method of detecting or quantitating endogenous wheat DNA in a test sample by a polymerase chain reaction, the method comprising: using a nucleic acid molecule in the sample or a nucleic acid molecule extracted from the sample as the template to amplify the nucleic acid molecule of a region consisting of the nucleotide sequence identified as SEQ ID NO: 2 or a partial sequence thereof with a primer pair capable of amplifying that region; and detecting or quantitating the amplified nucleic acid molecule;

(2) The method according to (1) above, wherein the region consisting of the partial sequence of the nucleotide sequence identified as SEQ ID NO: 2 is a region consisting of any one of the nucleotide sequences identified as SEQ ID NOs: 11 to 18;

(3) The method according to (1) above, wherein the aforementioned primer pair is a primer pair selected from a group consisting of: (i) a primer pair consisting of a nucleic acid molecule comprising the nucleotide sequence identified as SEQ ID NO: 3 and a nucleic acid molecule comprising the nucleotide sequence identified as SEQ ID NO: 4, (ii) a primer pair consisting of a nucleic acid molecule comprising the base sequence identified as SEQ ID NO: 5 and a nucleic acid comprising the base sequence identified as SEQ ID NO: 4, (iii) a primer pair consisting of a nucleic acid molecule comprising the nucleotide sequence identified as SEQ ID NO: 3 and a nucleic acid molecule comprising the nucleotide sequence identified as SEQ ID NO: 6, (iv) a primer pair consisting of a nucleic acid molecule comprising the nucleotide sequence identified as SEQ ID NO: 5 and a nucleic acid molecule comprising the nucleotide sequence identified as SEQ ID NO: 6, (v) a primer pair consisting of a nucleic acid molecule comprising the nucleotide sequence identified as SEQ ID NO: 3 and a nucleic acid molecule comprising the nucleotide sequence identified as SEQ ID NO: 7, (vi) a primer pair consisting of a nucleic acid molecule comprising the nucleotide sequence identified as SEQ ID NO: 3 and a nucleic acid molecule comprising the nucleotide sequence identified as SEQ ID NO: 8, (vii) a primer pair consisting of a nucleic acid molecule comprising the nucleotide sequence identified as SEQ ID NO: 5 and a nucleic acid molecule comprising the nucleotide sequence identified as SEQ ID NO: 8, (viii) a primer pair consisting of a nucleic acid molecule comprising the nucleotide sequence identified as SEQ ID NO: 5 and a nucleic acid molecule comprising the nucleotide sequence identified as SEQ ID NO: 7, (ix) a primer pair consisting of a pair of nucleic acids acid molecule with each nucleic acid molecule comprising a nucleotide sequence in common with at least 80% continuous nucleotide sequence of each nucleic acid molecule in the primer pairs in (i) to (viii) above;

(4) The method according to any one of (1) to (3) above, wherein each primer is the primer pair is a nucleic acid molecule having 15 to 40 bases long;

(5) The method according to any one of (1) to (4) above, wherein the region amplified in the above polymerase chain reaction is detected using a probe identified as SEQ ID NO: 9 or 10;

(6) A kit for detecting or quantitating an endogenous wheat DNA sequence in a test sample by the polymerase chain reaction, containing at least one primer pair of the primer pairs according to (3) above;

(7) Replicable DNA containing: a DNA sequence consisting of the nucleotide sequence identified as SEQ ID NO: 2 or a partial sequence thereof as endogenous DNA common to both genetically modified wheat and non-genetically modified wheat, and one or more DNA sequences comprising sequences that are specific to each strain of genetically modified wheat as genetically modified wheat-specific DNA;

(8) Replicable DNA containing: a DNA sequence consisting of a nucleotide sequence having at least 80% homology with the DNA consisting of the nucleotide sequence identified as SEQ ID NO: 2 or a partial sequence thereof as endogenous DNA common to both genetically modified wheat and non-genetically modified wheat, and one or more DNA sequences consisting of sequences that are specific to each strain of genetically modified wheat as genetically modified wheat-specific DNA;

(9) The method according to (7) or (8) above, wherein the DNA consisting of the partial sequence of the nucleotide sequence identified as SEQ ID NO: 2 is DNA consisting of any one of the nucleotide sequences identified as SEQ ID NOs: 11 to 18;

(10) Replicable DNA containing: DNA consisting of a sequence capable of being amplified by the polymerase chain reaction using any of the primer pairs according to (3) above as endogenous DNA common to both genetically modified wheat and non-genetically modified wheat, and one or more DNA sequences consisting of sequences that are specific to each strain of genetically modified wheat as genetically modified wheat-specific DNA;

(11) A method of determining a contamination rate of genetically modified wheat in a test sample, the method comprising: a step of preparing two or more types of concentration dilution series of solutions containing replicable DNA according to any one of (7) to (10) above, performing quantitative polymerase chain reactions for each, amplifying the above endogenous wheat DNA and at least one type of the above genetically modified wheat-specific DNA, and determining a calibration curve for each partial region; and a step of performing for the test sample a quantitative polymerase chain reaction under the same conditions as the above step for determining the calibration curves, and determining the number of the above endogenous wheat DNA molecules and the number of the above genetically modified wheat-specific DNA molecules present in the test sample using the above calibration curve;

(12) The method according to (11) above further comprising a step of determining the contamination rate of genetically modified wheat in the test sample by calculating a formula 100×NB using: the ratio A obtained by dividing the number of the above genetically modified wheat-specific DNA molecules by the number of the endogenous wheat DNA molecules present in the above test sample, and the ratio B obtained by dividing the number of DNA molecules specific to each strain of genetically modified wheat determined by performing quantitative polymerase chain reactions using standard seeds from each strain of genetically modified wheat by the number of endogenous wheat DNA molecules; and

(13) The method according to (11) or (12) above wherein amplification of the above endogenous wheat DNA is performed using at least one primer pair selected from the primer pairs according to (3) above.

EFFECT OF THE INVENTION

In accordance with the present invention it is possible to specifically detect and quantitate endogenous wheat DNA without cross reaction from other crops in a test sample such as a food material, processed food, and the like by PCR amplification of a partial region of the PRP gene.

Furthermore, it is possible to determine with good precision the contamination rate of each GMO strain in a test sample by quantitative PCR utilizing the standard reference material for detecting genetically modified wheat (hereinafter, sometimes referred to as "GM wheat") provided by the method herein.

DETAILED DESCRIPTION

Figure 1:
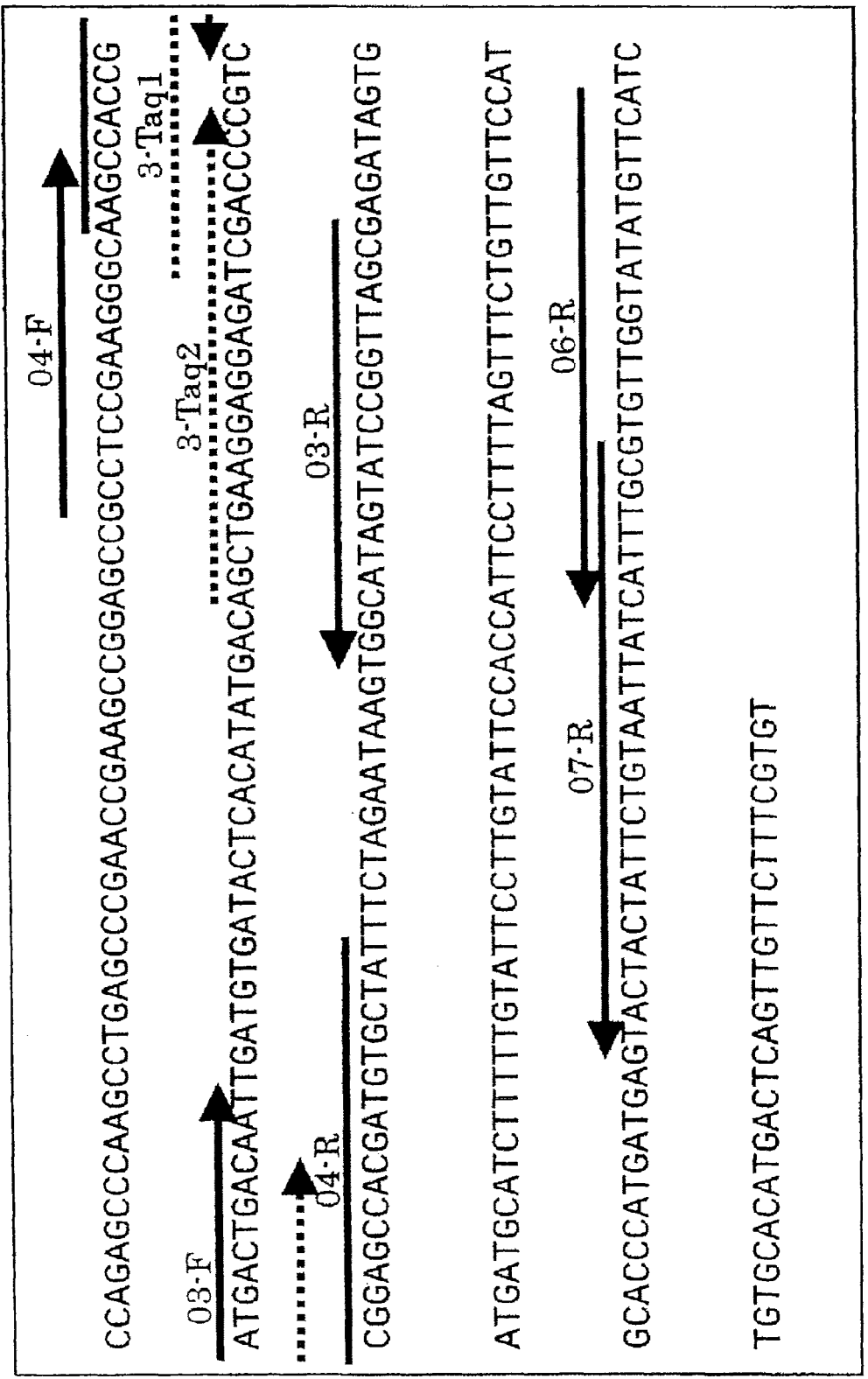
FIG. 1 shows the binding regions in SEQ ID NO: 2 of the primers identified as SEQ ID NOs: 3 to 8.

Below the meanings of terms used in this description are defined, and the present invention is described in detail.

In this description the term "wheat" refers to common wheat, durum wheat, and waxy wheat unless specifically stated otherwise.

The method of the present invention detects a specific part of the PRP gene (GeneBank Accession No. X52472, SEQ ID NO: 1) in the wheat genome, and more specifically, the region consisting of the nucleotide sequence identified as SEQ ID NO: 2 or a partial sequence thereof, as the endogenous wheat DNA sequence.

When the Wx012 region disclosed in Patent Document 1 and a plurality of partial regions of the PRP gene were amplified by PCR, it was found that in the various varieties of wheat the ratio of the Wx012 region amplification product to the amplification products of the various regions of the PRP gene varies between 1:1 and 1:3. Because it is thought that the ratios other than 1:1 are due to the presence of more than two regions on the PRP gene that are amplified by the same primer, these regions are not suitable for use as the endogenous wheat sequence used in the present invention. Therefore, the inventors continued their investigation and found that if a region consisting of the nucleotide sequence identified as SEQ ID NO: 2 or a partial sequence thereof (providing it is a region of 80 bases or more) is amplified, that amplification product and the Wx012 amplification product are obtained in a 1:1 ratio.

In addition, it was verified that the nucleotide sequence identified as SEQ ID NO: 2 or partial sequence thereof is detected in durum wheat as well. Therefore, it can be assumed that the PRP gene is present on wheat genome A or B. Since the wheat currently distributed on the market includes common wheat, durum wheat, waxy wheat, etc., as the endogenous wheat gene to be detected, it is preferred that the gene be universally present in these varieties of wheat and the amount present does not vary depending on the variety. In this regard, because genomes A and B must both be present in these varieties of wheat, the region consisting of the nucleotide sequence identified as SEQ ID NO: 2 is preferred as an endogenous wheat gene.

On the other hand, it was confirmed that a pseudogene that is extremely similar to the PRP gene exists. Therefore, in the process of amplifying the wheat genome in a processed food, if a primer that amplifies a partial sequence selected randomly from the entire length of the PRP gene is used, it is possible that the partial sequence of the pseudogene will also be amplified simultaneously. In other words, it is assumed that depending on the variety of wheat, there will be cases in which the quantity of amplified DNA per unit of wheat will inconsistent. However, the inventors have verified that if PCR is performed using a primer that amplifies the region consisting of the nucleotide sequence identified as SEQ ID NO: 2 or a partial sequence thereof, only that region of the PRP gene will be amplified with no pseudogene cross-reactivity.

Additionally, the region consisting of the nucleotide sequence identified as SEQ ID NO: 2 is an extremely short 330 by compared with the total genome length, and therefore it is possible to detect and quantitate endogenous wheat DNA from a sample of a processed food, etc., in which the DNA may be fragmented.

The partial sequence of the nucleotide sequence identified as SEQ ID NO: 2 is not particularly limited in the present invention, but preferably the length of the sequence will be at least 80 bases, and any one of the nucleotide sequences identified as SEQ ID NOs: 11 to 18 is preferred. These sequences can be amplified with PCR by suitably combining primers consisting of nucleic acid molecules comprising the nucleotide sequences identified as SEQ ID NOs: 3 to 8.

FIG. 1. shows the binding regions of the primers identified as SEQ ID NOs: 3 to 8 in SEQ ID NO: 2.

By altering the base length of the primers identified as SEQ ID NOs: 3 to 8 or by slightly altering the primer binding region, the amplified sequence becomes a region slightly displaced from the region comprising the nucleotide sequences identified in SEQ ID NOs: 11 to 18, but those regions are included within the "partial sequence of the nucleotide sequence identified as SEQ ID NO: 2" in the present invention. An example of such a region is a region having at least 80% or more, and preferably 90% or more, in common with the nucleotide sequences identified in SEQ ID NOs: 3 to 8.

The primer pair used in the PCR method in the present invention is not particularly limited provided it is a primer pair that can amplify a region consisting of the nucleotide sequence identified as SEQ ID NO: 2 or a partial sequence thereof, and the primer pair can be designed according to the basic rules for primer preparation in accordance with the nucleotide sequence of the region to be amplified. During that process unification of the Tm values of the primers should be kept in mind. The length of each primer should normally be 15 to 40 bp, and preferably 15 to 30 bp.

In the method of the present invention, if the primer pair to be used cross-reacts with a crop other than wheat, not only will the possibility of a false positive detection of wheat arise, but also it will be impossible to accurately quantitate the endogenous wheat DNA sequence in the test sample. The method of the present invention provides accurate information on the presence of wheat in a test sample such as a food material, processed food, etc., and the quantity thereof. Therefore, the primer pair for PCR used in the method of the present invention must not cross-react with other crops such as rice, barley, rye, oats, rapeseed, maize, foxtail millet, kibi millet, buckwheat, etc.

Examples of such primer pairs include (i) a primer pair consisting of a nucleic acid molecule comprising the nucleotide sequence identified as SEQ ID NO: 3 and a nucleic acid molecule comprising the nucleotide sequence identified as SEQ ID NO: 4, (ii) a primer pair consisting of a nucleic acid molecule comprising the nucleotide sequence identified as SEQ ID NO: 5 and a nucleic acid molecule comprising the nucleotide sequence identified as SEQ ID NO: 4, (iii) a primer pair consisting of a nucleic acid molecule comprising the nucleotide sequence identified as SEQ ID NO: 3 and a nucleic acid molecule comprising the nucleotide sequence identified as SEQ ID NO: 6, (iv) a primer pair consisting of a nucleic acid molecule comprising the nucleotide sequence identified as SEQ ID NO: 5 and a nucleic acid molecule comprising the nucleotide sequence identified as SEQ ID NO: 6, (v) a primer pair consisting of a nucleic acid molecule comprising the nucleotide sequence identified as SEQ ID NO: 3 and a nucleic acid molecule comprising the nucleotide sequence identified as SEQ ID NO: 7, (vi) a primer pair consisting of a nucleic acid molecule comprising the nucleotide sequence identified as SEQ ID NO: 3 and a nucleic acid molecule comprising the nucleotide sequence identified as SEQ ID NO: 8, (vii) a primer pair consisting of a nucleic acid molecule comprising the nucleotide sequence identified as SEQ ID NO: 5 and a nucleic acid molecule comprising the nucleotide sequence identified as SEQ ID NO: 8, (viii) a primer pair consisting of a nucleic acid molecule comprising the nucleotide sequence identified as SEQ ID NO: 5 and a nucleic acid molecule comprising the nucleotide sequence identified as SEQ ID NO: 7, (ix) a primer pair consisting of a pair of nucleic acid molecules with each nucleic acid molecule comprising a continuous nucleotide sequence having at least 80% or more, preferably 90% or more, and more preferably 85%, in common with the nucleotide sequence of a nucleic acid molecule in each primer pair in (i) to (viii) above. These primer pairs can specifically amplify a region comprising the nucleotide sequence identified as SEQ ID NO: 2 or a partial sequence thereof without cross-reacting with crops other than wheat.

In the method of the present invention the probe for detecting the region to be amplified by PCR is not particularly limited provided it can detect the amplification product quantitatively, but it is preferable to perform detection using a probe comprising the nucleotide sequence identified as SEQ ID NO: 9 or 10. These probes bind with high specificity to the amplification product, i.e., part of the region consisting of any of the nucleotide sequences identified as SEQ ID NOs: 11 to 18, and therefore they can detect the amplification product quantitatively. FIG. 1 shows the region to which a probe consisting of the nucleotide sequence identified as SEQ ID NO: 9 or 10 will bind.

The test sample used in the present invention is a food material or processed food that contains or may contain wheat, and examples include food materials and processed intermediate materials thereof such as raw grains of wheat, dried grains, wheat flour, mixed flour, and the like, and processed foods such as bread, noodles, and the like. The food material or food product includes not only human food products but also pet food and animal feed. Additionally, the term crops other than wheat refers to all crops that can be used as a food material or food raw material and include, for example, the aforementioned crops.

A test sample may be subjected to extraction of nucleic acid molecule as is or after pulverized, or may be subjected to extraction of nucleic acid molecule after washed, dried, and then pulverized. The nucleic acid molecule extracted from the test sample used in analysis is normally DNA. The DNA may be extracted by a publicly known desired method. At present many DNA extraction kits are on the market, and extraction can be performed using such a kit. For example, DNA can be extracted from a test sample using the DNeasy Plant Maxi Kit (QIAGEN GmbH) following the method of Koppel, et al., (Kopell, E. et al., Mitt. Gebiete Levensm, Hyg., 88, 164). The concentration of extracted DNA can be determined by an absorbance measurement, etc., and preferably is diluted to a concentration optimal for PCR and used.

In the method of the present invention PCR can be performed according to the conventional manner in consideration of the primers and DNA polymerase to be used. During that process, the PCR buffer solution, dNTP, reagents such as $MgCl_2$ and the like can be prepared, or a commercially available PCR kit can be used. One or two or more of the above primer pairs can be used in the PCR. An example of PCR conditions is 40 cycles with one cycle being 30 sec at 95° C., 30 sec at 63° C., and 30 sec at 72° C., with the final reaction being 7 min at 72° C. However, these conditions can be suitably varied in consideration of the Tm of the primers to be used, the length of the region to be amplified, concentration of template DNA, and the like.

Detection of the amplified nucleic acid molecule (PCR product) can be performed using a desired method that can identify a specific DNA fragment, more specifically, methods including agarose gel electrophoresis, acrylamide gel electrophoresis, capillary electrophoresis, hybridization, immunological methods, and the like. Generally, the result is verified by the migration pattern of the electrophoresis performed with the PCR product. For example, electrophoresis on a 0.8% agarose gel containing ethidium bromide can be performed and detection can be accomplished by band verification.

The present invention includes the primer pairs used in the aforementioned detection and quantitation method, and a kit containing those primer pairs. The primers can be produced by conventional methods. In addition to the primer pairs, the kit can contain other reagents, e.g., dNTP, $MgCl_2$, a polymerase such as TaqDNA polymerase, buffer solution (for example, Tris-HCl), glycerol, DMSO, DNA for a positive control, DNA for a negative control, distilled water, and the like. In the kit these reagents may be provided in individual packages, or two or more types of reagents may be provided as a mixture thereof. The concentrations of each of the reagents in the kit are not particularly limited in the present invention provided they are within a permissible range for performance of the PCR method in the present invention. Information on optimal PCR conditions and the like may also be included in the kit, or the kit may contain only the primer reagents.

The present invention provides a standard reference material useful when measuring the GM wheat contamination rate by quantitative PCR. This standard reference material is made by ligating endogenous DNA common to both non-GM wheat and GM wheat and DNA specific to at least one GM wheat on a single replicable DNA molecule. DNA comprising a nucleotide sequence identified as any one of SEQ ID NOs: 11 to 18 can be used as the aforementioned partial sequence.

The standard reference material of the present invention may also be a replicable DNA molecule comprising DNA consisting of a nucleotide sequence having at least 80% homology with DNA consisting of the nucleotide sequence identified as SEQ ID NO: 2 or a partial sequence thereof as endogenous DNA.

The replicable DNA used as the standard reference material is not particularly limited in the present invention provided endogenous DNA and DNA specific to a strain of GM wheat can be inserted thereinto, and a commercially available vector such as a pBR-series vector (e.g., pBR322, pBR328, etc.), a pUC-series vector (pUC19, pUC18, etc.), a λphase series vector (λgt10, λgt11, etc.), or a modified form thereof can be used.

In the case of detecting GM wheat, it is not only necessary to amplify and detect a foreign DNA sequence inserted into the normal wheat genome by genetic engineering, but also to amplify a region containing the endogenous sequences upstream and downstream of the foreign DNA. Because GMO are prepared in other crops as well by inserting the same foreign DNA sequence, if the foreign DNA sequence alone is detected, it is still impossible to judge whether it originates in GM wheat or in another genetically modified crop. Therefore, primers for detecting a sequence specific to a GMO strain must be primers that can amplify the region containing the foreign DNA sequence inserted into each strain of GM wheat, and also the upstream and downstream endogenous sequences. These kinds of primers are prepared, for example, by following the aforementioned method of Koppel et al., reported for soybeans, the method of Wurz et al., (Wurz, A. et al.; 2nd Status report. BgW, BgVV-Heft, 1/199797,118), or a method based thereon. The sequence specific to each strain of GM wheat inserted in the aforementioned standard reference material is selected from DNA sequences that can be amplified by these primers.

After the endogenous wheat DNA and the GM wheat-specific DNA to be inserted into the standard reference material are determined, PCR is performed using the normal wheat genome or GM wheat genome as a template, the endogenous DNA and the GM wheat-specific DNA are cloned, and by cleaving the cloned DNA fragments and the cloning site of the aforementioned replicable DNA with the same restriction enzyme, the DNA fragments can be ligated into the cleavage site in the replicable DNA. Publicly known restriction enzymes can be suitably selected and used, and examples include EcoRI, SpeI, EcoRV, SmaI, SacI, NotI, HindIII, XhoI, etc.

If two or more types of dilution series of the above solution containing the standard reference material are prepared and quantitative PCR is performed on each, it is possible to determine calibration curves for the partial regions of both the endogenous wheat DNA sequence and the GMO-specific DNA sequence. The standard reference material of the present invention can also be used as a positive control for the endogenous wheat DNA sequence and GMO-specific DNA sequence in qualitative PCR.

The present invention includes a method of determining the GM-wheat contamination rate in a test sample by PCR using the above standard reference material. This method comprises the step of determining the calibration curve of a specific sequence using the above standard reference material, and the step of performing a quantitative polymerase chain reaction under the same conditions used when determining the calibration curve, amplifying the partial region of the endogenous wheat DNA sequence and the partial region of the GM wheat-specific DNA sequence, and by using the calibration curves, determining the number of molecules of the partial region of the endogenous wheat DNA sequence and of the partial region of the GM wheat-specific DNA sequence.

When calculating the contamination rate of GM wheat in a test sample, first ratio A is determined: Ratio A is obtained by dividing the number of molecules of the partial region of the GM wheat-specific DNA sequence by the number of molecules of the partial region of the endogenous wheat DNA sequence. Then ratio B is determined: Ratio B is obtained by dividing the number of molecules of the partial region of the DNA sequence specific to each strain of GM wheat, which is obtained by performing quantitative PCR using a standard grain of genetically modified wheat, by the number of molecules of the partial region of the endogenous wheat DNA sequence. Finally, it is possible to perform the step of determining the contamination rate of genetically modified wheat in the test sample by calculating the formula 100×A/B. The above ratio B is called the "internal standard ratio" in Non-Patent Document 1, and it is the ratio signifying (recombinant gene)/(endogenous gene) in the DNA extracted from the grains of each pure GM strain.

Each PCR step performed in the method of determining the GM wheat contamination rate in the present invention can be performed separately, but they may be performed simultaneously. It is preferred that each PCR step be performed under conditions wherein the nucleic acid molecule amplification reaction occurs at approximately the same rate as in the PCR performed to prepare the calibration curves. Examples of such conditions are ones wherein the temperatures and cycles are the same as in the PCR performed to prepare the calibration curves. The calculation of the GM wheat contamination rate may be performed by measuring the amounts of endogenous DNA and recombinant DNA separately and calculating those measured results, but it is also possible to perform amplification with a real-time PCR apparatus following the method described in Non-Patent Document 1 and calculate the GM wheat contamination rate thereby. In the present invention the term "recombinant DNA" refers to an arbitrary foreign DNA molecule artificially inserted into wheat, and examples include DNA of a region encoding a foreign gene, an untranscribed or untranslated region, linker region, or vector part.

EXAMPLES

The present invention is explained in greater detail through the following examples, but the present invention is by no means limited thereto, and a variety of embodiments thereof are possible. Therefore, it should be understood that the present invention encompasses all such embodiments thereof provided they are in accordance with the concepts disclosed by the description and drawings herein.

The following samples, reagents, and devices are used in examples below.

(1) Samples

Wheat (*Triticum aestivum*): dried seeds of the following varieties were used: Hank, Scarlet, Tara, Yecora Rojo, Finch, Lewjain, Rod, Weatherford, Estica, Buchanan, Finley, Garland, TAM 107, Declo, Hatton, Morgan, Neely, Ramp, Amidon, Ernest, McNeal, AC-Barrie, AC-Splendor, CDC-Teal, Laura, Nishikaze, Nishihonami, Chikugo Izumi, Tsugaru HDC, Shirogane, Shirasagi, Bihoro HDN, Hokushin, Bandowase, Kita HDI, Norin No. 61, Hatsumochi, Mochiotome, Kanto 107, and Bai Huo.

Durum wheat (*Triticum durum*): dried seeds of the following variety were used: AC Navigator.

Maize (*Zea mays*): dried seeds of the following variety were used: Dent corn.

Soybeans (*Glycine max*): dried seeds of the following variety were used: descendent variety of genetically modified soybean Roundup® Ready Soy.

Rice (*Oryza sativa*): dried seeds of the following variety were used: Koshihikari.

Barley (*Hordeum vulgare*): dried seeds of the following variety were used: Benkei.

Oats (*Avena sativa*): dried seeds of the following variety were used: Commercial product.

Rye (*Secale cereale*): dried seeds of the following variety were used: Commercial product.

Rapeseed (*Brassica napus*): dried seeds of the following variety were used: Canola.

Foxtail millet (*Setaria italica* Beauvois): dried seeds of the following variety were used: Mochiawa.

Kibi millet (*Panicum miliaceum* Panicum): dried seeds of the following variety were used: Mochikibi.

Sorghum (*Sorghum subglabrescens*): dried seeds of the following variety were used: Commercial product.

Buckwheat (*Fagopyrum esculentum*): dried seeds of the following variety were used: Domestic variety.

(2) Reagents (2-1) The following reagents were used for the extraction of DNA from the samples.

Sodium lauryl sulfate (SDS) (special reagent grade) (Sigma Chemical Co.)

QIAGEN DNeasy Plant Maxi Kit (QIAGEN GmbH)

QIAGEN DNeasy Plant Mini Kit (QIAGEN GmbH)

The following reagents were used for DNA electrophoresis.

Acetic acid (special reagent grade) (Wako Pure Chemical Industries, Ltd.)

Tris (hydroxymethyl) aminomethane (Tris) (special reagent grade) (Sigma Chemical Co.)

Ethylenediaminetetraacetate (EDTA) (special reagent grade) (Sigma Chemical Co.)

Agarose powder "TaKaRa LO3" (TaKaRa Shuzo Co., Ltd.)

Ethidium bromide (Sigma Chemical Co.)

Bromophenol blue (Sigma Chemical Co.)

Xylene cyano) (Sigma Chemical Co.)

DNA marker "1 kb ladder" (New England Biolabs Inc.)

DNA marker "100 by ladder" (New England Biolabs Inc.)

(2-2) The following reagents were used for qualitative PCR.

DNA polymerase "AmpliTaq Gold" (Applied Biosystems)

×10 PCR Buffer II (Applied Biosystems)

(2-3) The following reagents were used for plasmid preparation and purification.

DNA polymerase "AmpliTaq Gold" (Applied Biosystems)

×10 PCR Buffer II (Applied Biosystems)

DNA polymerase "KOD" (TOYOBO Co., Ltd.)

×10 PCR Buffer II (TOYOBO Co., Ltd.)

TOPO TA Cloning Kit with TOP10F' Cells (Invitrogen Co.)

Yeast extract (Difco Laboratories)

Tryptone Peptone (Difco Laboratories)

NaCl (special reagent grade) (Wako Pure Chemical Industries, Ltd.)

Agarose powder (TAKARA BIO, Inc.)

D[-]-α-Aminobenzylpenicillin (Ampicillin) Sodium Salt (Sigma Chemical Co.)

QIAGEN Plasmid Maxi Kit (QIAGEN GmbH)

Ethanol (special reagent grade) (Wako Pure Chemical Industries, Ltd.)

2-Propanol (special reagent grade) (Wako Pure Chemical Industries, Ltd.)

Tris(hydroxymethyl)aminomethane (Tris) (special reagent grade) (Sigma Chemical Co.)

Ethylenediaminetetraacetate (EDTA) (special reagent grade) (Sigma Chemical Co.)

Restriction enzyme "EcoRI" (TaKaRa Shuzo CO., LTD.)

Restriction enzyme "SacI" (New England Biolabs Inc.)

Restriction enzyme "XbaI" (New England Biolabs Inc.)

Calf Intestinal Alkaline Phosphatase (Invitrogen)

Phenol (special reagent grade) (Wako Pure Chemical Industries, Ltd.)

Chloroform (special reagent grade) (Wako Pure Chemical Industries, Ltd.)

Isoamyl alcohol (special reagent grade) (Wako Pure Chemical Industries, Ltd.)

(2-4) The following reagent was used for quantitative PCR.

TaqMan Universal PCR Master Mix (Applied Biosystems)

(3) Equipment (3-1) The following equipment was used for the extraction of DNA from the samples.

Pulverizer "Multi Beads Shocker MB301" (Yasui Kikai Co., Ltd.)

(3-2) The following equipment was used for DNA electrophoresis.
Electrophoresis device "Mupid 2" (Advance Co., Ltd.)
(3-3) The following equipment was used for qualitative PCR.
Thermal cycler "PTC-200" (MJ Research Inc.)
(3-4) The following equipment was used for quantitative PCR.
Quantitative PCR device "ABI PRISM 7700 Sequence Detector System" (Applied Biosystems)
Synthesis of the primers and probes was consigned to Operon Biotechnologies.

Example 1

Plasmid Construction

Genomic DNA was extracted from grains of the Ernest cultivar of wheat, and PCR was performed using this DNA as a template. Table 1 shows the targets of amplification, and amplification was performed for two types of endogenous wheat gene candidates (PRP gene and Waxy gene), and for the RRS gene as a hypothetical GM wheat gene. Table 2 shows the primers that were used. As explained below, the RRS gene is a Roundup® resistant gene.

TABLE 1

| Gene | General Name | Size (bp) |
|------|--------------|-----------|
| PRP  | Proline rich protein | 259 |
| Waxy | WaxyD1 | 529 |
| RRS  | 5-enolpyruvylshikimate-3-phosphate synthase | 1886 |

TABLE 2

| Gene | Name | Sequence | Amplicon size |
|------|------|----------|---------------|
| PRP | prp04-F | 5'-GCCTCCGAAGGGCAAGC-3' (SEQ ID NO: 5) | 259 bp |
|     | prp06-R | 5'-GAACATATACCAACACGCAAATG-3' (SEQ ID NO: 6) | |
| RRS | RRS-F | 5'-TGGAAAAGGAAGGTGGCTCCTAC-3' (SEQ ID NO: 23) | 1919 bp |
|     | RRS-R | 5'-GGGAATTGGATCCGGTACCGA-3' (SEQ ID NO: 24) | |
|     | RRS Sac-F | 5'-AGAGCTCTGGAAAAGGAAGGTGGCTCCTAC-3' (SEQ ID NO: 25) | 1926 bp |
|     | RRS Sac-R | 5'-CGGAATTCGATCCGGTACCGA-3' (SEQ ID NO: 26) | |
| Waxy | Wx-F | 5'-TTTTGTTGTGCCGCTTGCCT-3' (SEQ ID NO: 27) | 529 bp |
|      | Wx-R | 5'-AGTTTAGCGCGTCACAGACTCA-3' (SEQ ID NO: 28) | |
|      | Wx Xba-F | 5'-TCTCTAGATTTTGTTGTGCCGCTTGCCT-3' (SEQ ID NO: 29) | 545 bp |
|      | Wx Wba-R | 5'-TCTCTAGAGTTTAGCGCGTCACAGACTCA-3' (SEQ ID NO: 30) | |

Next, PCR was performed again using the obtained amplified DNA as a template with a primer having restriction enzyme cleavage site added thereto. After digestion with the restriction enzyme had been performed on the obtained amplified DNA, the purified fragments were ligated to pUC19 vectors, and E. coli were transformed thereby. Alternatively, TA cloning into a pCR4 vector was performed. After the insertion fragments were verified by restriction enzyme mapping, the entire sequences of the obtained clones were verified by sequencing.

After restriction enzyme digestion of each of the TA clones, the purified fragments were ligated to pUC19 vectors, and E. coli were transformed thereby.

The plasmids were extracted from the transformants and purified, and the sequences were verified.

Plasmids were constructed according to the process described above. More specifically, the WaxyD1 region amplified with a primer having a restriction enzyme cleavage site added thereto was digested with XbaI, and then it was ligated to pUC19 that had been subjected to XbaI digestion in the same manner and dephosphorylated to construct pWIG01.

TA cloning was performed once on the PCR-amplified RRS gene, the obtained plasmid pRRS was digested with EcoRI and SacI, and the RRS fragment was purified. In the same manner, pWIG01 was digested with EcoRI and SacI, and after the plasmid was purified, the RRS fragment was ligated thereto to construct pWIG02.

TA cloning was performed once on the PCR-amplified PRP gene, the obtained plasmid pPRP was digested with EcoRI, and the PRP fragment was purified. In the same manner, pWIG02 was digested with EcoRI, and dephosphorylated, and then the PRP fragment was ligated thereto to construct pWIG03.

Sequencing of the constructed plasmids was performed and the insertion sequences were verified. All verified sequences matched the target sequences.

The procedure used in Examples 1 to 3 is specifically described below.

(1) Restriction Enzyme Digestion

The procedures were performed following the manuals for each restriction enzyme. More specifically, each DNA solution was mixed with the restriction enzyme, distilled water, and the ×10 buffer for the enzyme, and the reaction was normally carried out for 2 h at 37° C.

(2) DNA Fragment Purification Following Digestion

The DNA fragments were separated using agarose gel electrophoresis. The kit from QIAGEN was used for purification from the gel. In other words, the gel containing the target DNA was heated and dissolved, and the DNA was bound to a silica film. After the silica film was rinsed with a solution containing ethanol, etc., the DNA was eluted with distilled water.

(3) Dephosphorylation of Restriction Enzyme-digested Plasmids

The plasmids were subjected to restriction enzyme digestion and desalted. Then the plasmids were mixed with calf intestinal alkaline phosphatase (CIAP, GIBCO BRL) and a dedicated buffer, and reacted for 30 min at 37° C. The CIAP was deactivated after the reaction by treatment with phenol, and the dephosphorylated plasmid was recovered by ethanol precipitation.

(4) DNA Ligation

A DNA ligation kit (TAKARA BIO INC.) ver. 2 was used. More specifically, the target DNA was mixed into solution, an equivalent volume of the kit reaction solution (solution I) was added, and the mixture was let stand for 30 min at 16° C. to perform DNA ligation.

(5) Transformation

E. coli DH5α competent cells (Toyobo Co., Ltd.) were used. A thawed suspension of 10 to 50 μL of competent cells was mixed with DNA and let stand on ice for 30 min, and after a heat shock for 50 sec at 42° C., the mixture was placed on ice again, 450 μL of SOC medium warmed to 37° C. was added after 2 min had elapsed, and the mixture was incubated for 1 h at 37° C. The incubate was then spread at 100 μL/plate on Circlegrow® Amp+ medium plates and cultured for 16 h at 37° C.

(6) Culturing

Culturing for the purpose of plasmid purification was performed using Circlegrow® medium. Ampicillin resistance was used for the plasmid production selection pressure, and a final concentration of 100 μg/mL of ampicillin was used. Culturing was performed for 14 to 16 h at 37° C. using a test tube shaker.

(7) PCR

AmpliTaq Gold polymerase from Applied Biosystems was used. The composition shown in Table 3 was used as the reaction composition. The reaction was performed under the conditions shown in Table 4.

TABLE 3

|  | μL |
|---|---|
| 10 × Buffer | 2.5 |
| 25 mM MgCl$_2$ | 1.5 |
| 2.5 mM dNTP | 2.0 |
| Primer pair | 2.5 |
| 5 u/mL Taq | 0.25 |
| MQ H$_2$O | 15.75 |
| 50 ng/μL DNA | 0.5 |
| Total | 25.0 |

TABLE 4

| Step | Temp. (° C.) | Time (min) | Cycle No. |
|---|---|---|---|
| 1 | 95 | 10 min |  |
| 2 | 95 | 30 sec | 40 |
| 3 | 60 | 30 sec |  |
| 4 | 72 | 2 min |  |
| 5 | 72 | 7 min |  |
| 6 | 10 | ad infinitum |  |

(8) TA Cloning

TA cloning was performed using the TOPO TA cloning system from Invitrogen according to the manufacturer's manual.

(9) DNA Sequencing

DNA sequencing was performed using a model CEQ8000 from Beckman Coulter according to the manufacturer's manual. DTCS Quick Start Master Mix from Invitrogen was used as the kit.

(10) Real-time PCR SYBR Procedure

Real-time PCR was performed using a kit from TAKARA BIO (TAKARA SYBR® Premix EX TAQ™ (a thermostable DNA polymerase which possesses a 3' to 5' exonuclease activity) (Perfect Real Time) Code No.: RR041A).

1) The template DNA (plasmid) was diluted in accordance with Table 5 (A 5 ng/μL solution of ColE1 was used for the dilution).

2) Unknown DNA was prepared at 4 points in a dilution series ranging from 10-fold to 2-fold (A 5 ng/μL solution of ColE1 was used for the dilution).

3) The Master Mix was prepared for each primer according to Table 5.

4) The Master Mix and template DNA were mixed.

5) The reaction was initiated under the conditions shown in Table 6.

TABLE 5

| Step | Temp. | Time | Cycle | Ramp time |
|---|---|---|---|---|
| 1 | 50° C. | 2 min | 1 | Auto |
| 2 | 95° C. | 10 min | 1 | Auto |
| 3 | 95° C. | 5 sec | 40 | Auto |
|  | 60° C. | 30 sec |  | Auto |
| 4 | 95° C. | 15 sec | 1 | Auto |
| 5 | 60° C. | 20 sec | 1 | Auto |
| 6 | 95° C. | 15 sec | 1 | 20 min |
| 7 | 20° C. | 1 min | 1 | Auto |

TABLE 6

|  | Conc. | μL |
|---|---|---|
| SYBR Premix |  | 5 |
| Primer pair | 5 μM each | 0.4 |
| ROX | ×50 | 0.2 |
| MQ H$_2$O |  | 0.4 |
| template |  | 4.0 |
| Total |  | 10.0 |

(11) Real-Time PCR TaqMan® Procedure

Real-time PCR was performed using a kit from TAKARA BIO (TAKARA Premix EX TAQ™ (a thermostable DNA polymerase which possesses a 3' to 5' exonuclease activity) (Perfect Real Time) Code No.: RR039A).

1) The genomic DNA of each variety was used as the template without dilution.

2) The Master Mix was prepared by mixing with Premix, ROX, primer, and probe according to Table 7.

3) The Master Mix at 16 μL/well was mixed with template DNA at 4 μL/well.

4) The reaction was initiated under the conditions shown in Table 8.

TABLE 7

|  | Conc. | μL |
|---|---|---|
| Premix | ×2 | 10 |
| ROX | ×50 | 0.4 |
| Probe | 10M | 0.8 |
| Primer pair | 5M each | 0.8 |
| H$_2$O |  | 4.0 |
| Total |  | 16.0 |

TABLE 8

| Step | Temp. | Time | Cycle | Ramp time |
|---|---|---|---|---|
| 1 | 50° C. | 2 min | 1 | Auto |
| 2 | 95° C. | 10 min | 1 | Auto |
| 3 | 95° C. | 5 sec | 40 | Auto |
|  | 60° C. | 30 sec |  | Auto |
| 4 | 20° C. | 1 min | 1 | Auto |

The template DNA (plasmid) was diluted in accordance with Table 9 (A 5 ng/μL solution of ColE1 was used for the dilution).

TABLE 9

|  | Stock solution conc. | 2nd stock solution conc. | Well | | | | | |
|---|---|---|---|---|---|---|---|---|
|  | $10^7$ copy/μl | $10^5$ copy/μl | 2 | 3 | 4 | 5 | 6 | 7 | 8 |
| Stock solution volume (μL) | → | 4 | | 20 | | 20 | | 20 | |
| Diluted solution volume (μL) | | 396 | | 180 | | 180 | | 180 | |
| Stock solution volume (μL) | | | 63.2 | | 20 | | 20 | | 20 |
| Diluted solution volume (μL) | | | 136.8 | | 180 | | 180 | | 180 |
| Final conc. copy/μL | | $10^5$ | $3.16 \times 10^4$ | $10^4$ | $3.16 \times 10^3$ | $10^3$ | $3.16 \times 10^2$ | $10^2$ | $3.16 \times 10^1$ |

(12) Pulverization of Seeds (Small Quantity)

The aforementioned pulverizer, a Multi Beads Shocker MB301, was used.

1) One seed was placed in a 2 mL tube, a metal cone was added, and the tube was capped.
2) Pulverization was performed twice at 2000 rpm for 10 sec.
3) DNA was directly extracted from the pulverized powder.

(13) Pulverization of Seeds (Large Quantity)

A mill was used for pulverization.

1) Seeds (30 g) were placed in the mill and the lid was attached.
2) Pulverization was performed twice for 30 sec.
3) The pulverized powder was stored.

(14) Preparation of Qenomic DNA

A kit from QIAGEN (QIAGEN Plant Mini Kit) was used. The procedure was performed according to the kit manual.

1) 400 μL of AP1 solution and 4 μL of RNase A were added to the pulverized seed, and the mixture was agitated.
2) The mixture was incubated for 10 min at 65° C., and mixed 2 or 3 times during incubation.
3) 130 μL of AP2 was added, and after agitation, the mixture was let stand on ice for 10 min.
4) Centrifugal separation (15,000 rpm=20,000 g, 5 min, room temperature) was performed.
5) The entire volume of supernatant was placed in a QIAshredder, and centrifugal separation (15,000 rpm, 2 min, room temperature) was performed.
6) The pass-through supernatant from decanting was transferred to a separate container, 1.5 volumes (675 μL) of AP3/E was added, and the mixture was agitated.
7) Half the volume was applied to a spin column, and centrifugal separation (10,000 rpm, 1 min, room temperature) was performed.
8) The flow-through was discarded, and the same treatment was performed on the residual amount.
9) The column was placed in a new tube, 500 μL of AW was added, and centrifugal separation (10,000 rpm, 1 min, room temperature) was performed.
10) After retreatment, the flow-through was discarded, and centrifugal separation (15,000 rpm, 2 min, room temperature) was performed.

The column was placed in a fresh 1.5 mL tube, 50 μL of AE was added, and after the mixture was let stand for 5 min at room temperature, centrifugal separation (10,000 rpm, 1 min, room temperature) was performed.

Thereafter, the above step was repeated.

(15) DNA Quantitation

A GeneSpec was used as the instrument, and DNA quantitation was performed according to the instrument manual.

The cell was 5 mm, the dilution rate was 1-fold, and the control was kit elution solution (AE).

Example 2

Verification of PCR Amplification Rate

Figure 2:
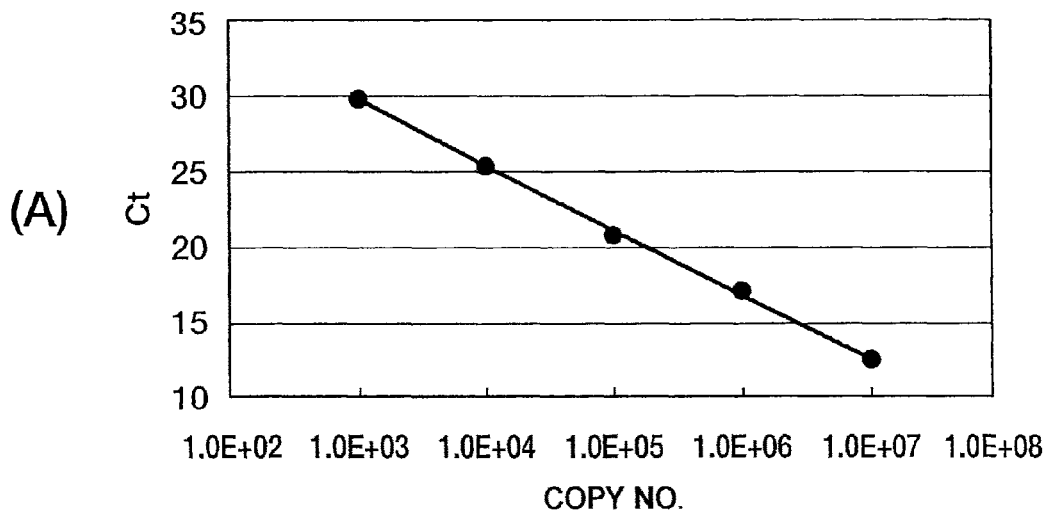
FIG. 2 shows the amplification curve and melting curves when real-time PCR is performed by the SYBR procedure using the standard plasmid pWIG03 as a template on the amplified regions of the PRP and the Waxy genes.
Figure 2:
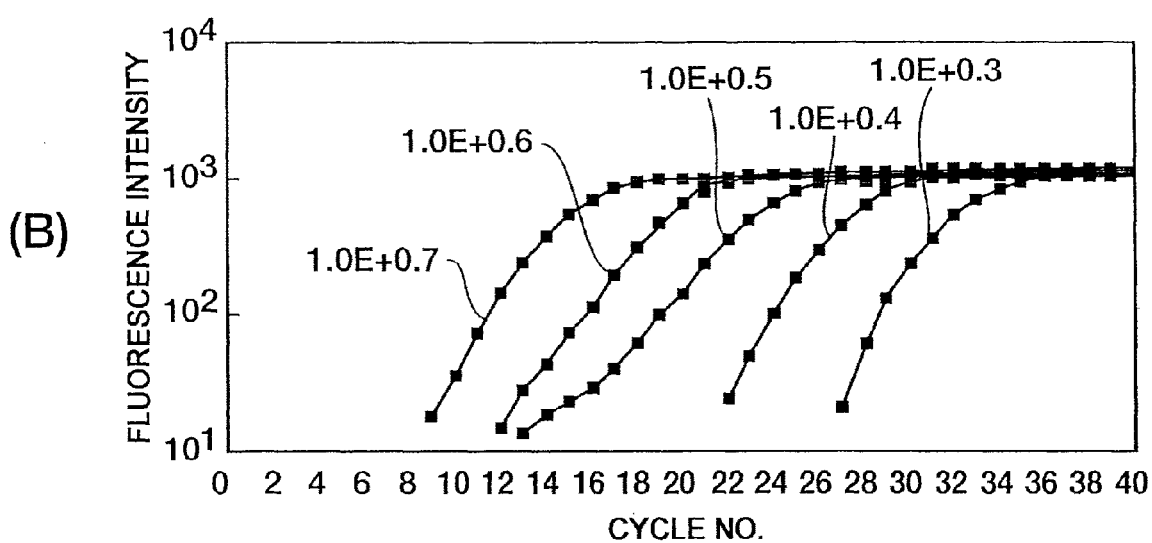
Figure 2:
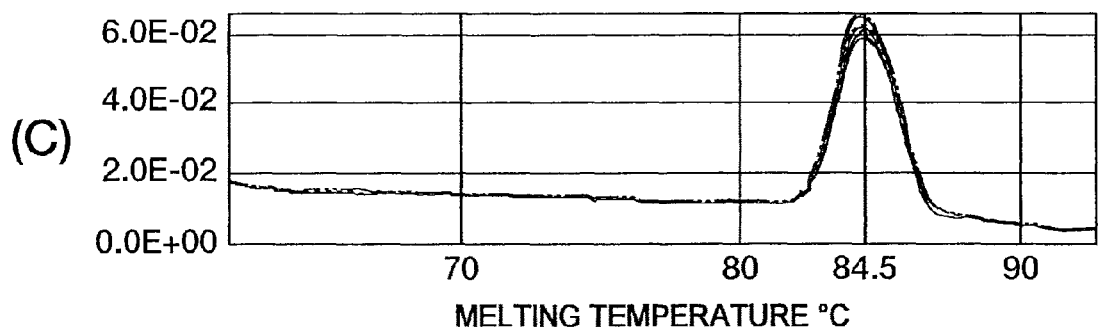

For the amplification regions of the PRP and Waxy genes, real-time PCR was performed by the SYBR procedure using the standard plasmid pWIG03 as a template. Template concentration-dependent amplification was observed for all genes and all PCR regions under the same conditions. According to the melting curves of the amplification products, each amplification product had a main peak having a high-melting point, and no formation of primer dimers was observed. FIG. 2 shows the amplification curve and melting curves. Table 10 shows a listing of the primer sequences used in Example 2 and thereafter.

TABLE 10

| Gene Name | Sequence | Amplicon size (bp) |
|---|---|---|
| PRP | prp03-F 5'-aag cca ccg atg act gac aat-3' (SEQ ID NO: 3)<br>prp07-R 5'-cgc aaa tga taa tta cag aat agt agt ac-3' (SEQ ID NO: 4) | 231 (SEQ ID NO: 11) |
|  | prp04-F 5'-gcc tcc gaa ggg caa gc-3' (SEQ ID NO: 5)<br>prp07-R 5'-cgc aaa tga taa tta cag aat agt agt ac-3' (SEQ ID NO: 4) | 244 (SEQ ID NO: 12) |
|  | prp03-F 5'-aag cca ccg atg act gac aat-3' (SEQ ID NO: 3)<br>prp06-R 5-gaa cat ata cca aca cgc aaa tg-3' (SEQ ID NO: 6) | 246 (SEQ ID NO: 13) |
|  | prp04-F 5'-gcc tcc gaa ggg caa gc-3' (SEQ ID NO: 5)<br>prp06-R 5-gaa cat ata cca aca cgc aaa tg-3' (SEQ ID NO: 6) | (SEQ ID NO: 14) |
|  | prp03-F 5'-aag cca ccg atg act gac aat-3' (SEQ ID NO: 3)<br>prp03-R 5'-cgc taa ccg gat act atg cca-3' (SEQ ID NO: 7) | 121 (SEQ ID NO: 15) |
|  | prp03-F 5'-aag cca ccg atg act gac aat-3' (SEQ ID NO: 3)<br>prp04-R 5'-ata gca cat cgt ggc tcc gg-3' (SEQ ID NO: 7) | 88 (SEQ ID NO: 16) |

TABLE 10-continued

| Gene Name | Sequence | Amplicon size (bp) |
|---|---|---|
| | prp04-F 5'-gcc tcc gaa ggg caa gc-3' (SEQ ID NO: 5)<br>prp04-R 5'-ata gca cat cgt ggc tcc gg-3' (SEQ ID NO: 8)<br>prp01-F 5'-gcg aca ccc cat cca ctt ta-3' (SEQ ID NO: 19)<br>prp01-R 5'-cac ggc aag gag gct gtg-3' (SEQ ID NO: 20) | 101 (SEQ ID NO: 17) |
| Waxy | Wx012-F 5'-ggt cgc agg aac aga ggt gt-3' (SEQ ID NO: 21)<br>Wx012-R 5'-ggt gtt cct cca ttg cga aa-3' (SEQ ID NO: 22) | 102 (SEQ ID NO: 18) |

Example 3

Search for Amplified Regions in PRP Gene

A search for regions in the PRP gene of which the detected quantity does not vary depending on the variety of wheat was made. The Waxy gene was used as a positive control, and a search for regions that give the detective amount equivalent of Wx012 amplified regions was made. The primer pairs used were: PRP01-F and PRP01-R, PRP03-F and PRP03-R, and PRP03-F and PRP07-R shown in Table 10. Real-time PCR was performed by the SYBR procedure using DNA extracted from wheat seeds as a template.

Figure 3:
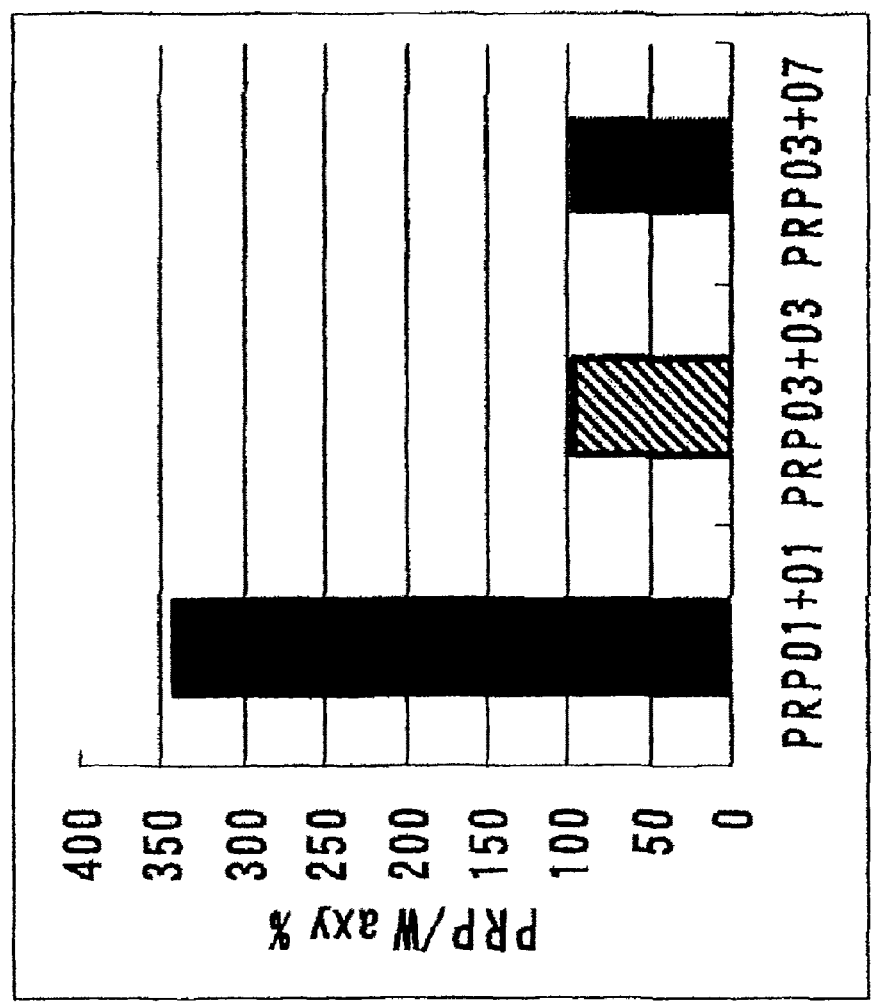
FIG. 3 shows the results when real-time PCR was performed by the SYBR procedure using DNA extracted from wheat seeds as the template and using the primer pairs of PRP01-F and PRP01R, PRP03-F and PRP03-R, and PRP03-F and PRP07-R shown in Table 10.

The results are shown in FIG. 3. When the primer pairs of PRP03-F and PRP03-R, and PRP03-F and PRP07-R were used, it was confirmed that the detected amount of PRP was approximately the same as that of Wx012. However, when PRP01-F and PRP01-R were used as primer, the detected amount was approximately three times larger than Wx012.

From this finding, it was confirmed that a gene homologous to PRP gene is present at the upstream region of the PRP gene (the amino-terminus side as a post-translation protein sequence) in wheat DNA, and this upstream region is undesirable as endogenous DNA.

Example 4

Probe Search

From the investigations in Examples 1 to 3 it was confirmed that the region from PRP04-F to PRP06-R is preferred as a region of an endogenous wheat gene for a PCR amplification. Probes were then designed that were suitable to each type of primer pair for this region. For design of the probes the Primer Express or Primer3 primer design assistance software was used (The development of Primer3 and the Primer3 web site was funded by Howard Hughes Medical Institute and by the National Institutes of Health, National Human Genome Research Institute. Under grants R01-HG00257 (to David C. Page) and P50-HG00098 (to Eric S. Lander). A fluorescently labeled probe was synthesized from the designed probe sequence. The 5' end was labeled with FAM and the 3' end was labeled with TAMRA as fluorescent labels. Using these probes, real-time PCR conditions were established for the TaqMan procedure using the standard plasmid as a template. After optimal conditions were determined, a comparison of various primer (see Table 10) and probe combinations was performed. Satisfactory amplification was obtained with each of the combinations, and the detection efficiency was approximately the same.

Figure 4:
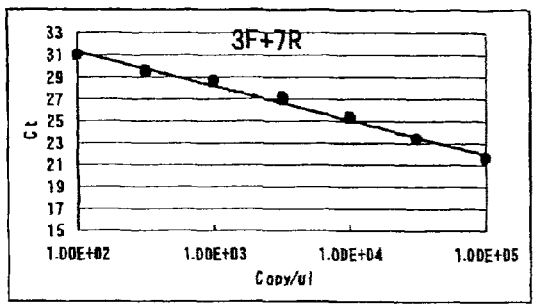
FIG. 4 shows the detection efficiency by real-time PCR using the combinations of primers shown in Table 11.
Figure 4:
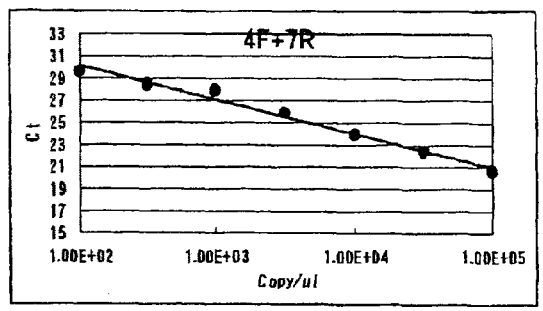
Figure 4:
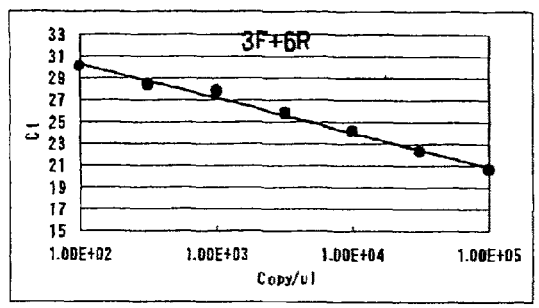
Figure 4:
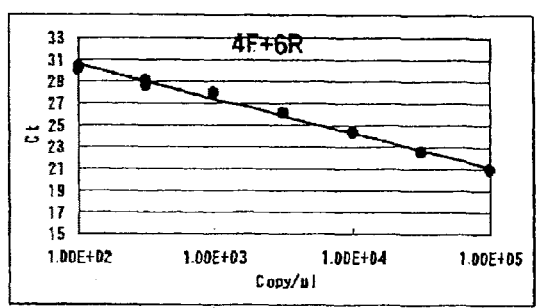
Figure 4:
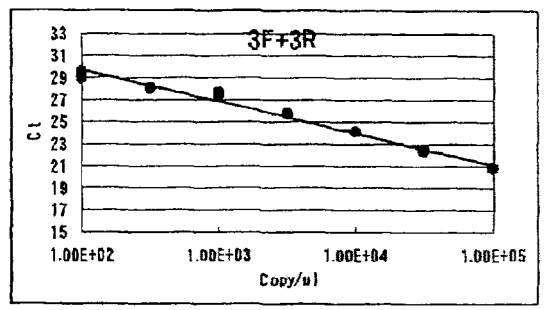
Figure 4:
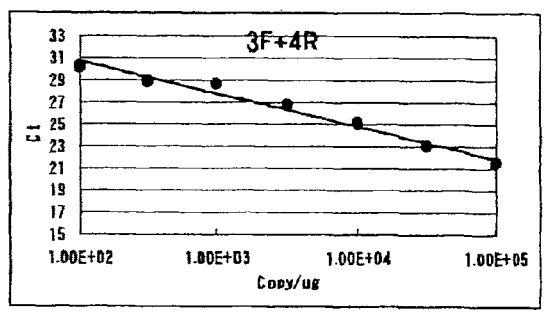
Figure 4:
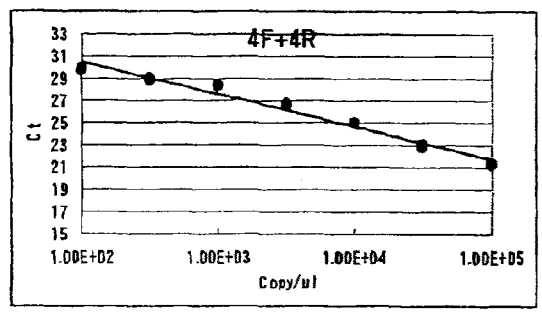

Table 11 shows the sequences of the designed probes. FIG. 4 shows the results obtained using each type of primer.

TABLE 11

| Probe name | Sequence |
|---|---|
| PRP-Taq1 | 5'-TCGACCCCGTCCGGAGCCAC-3'<br>(SEQ ID NO: 9) |
| PRP-Taq2 | 5'-AGCTGAAGGAGGAGATCGACCCC-3'<br>(SEQ ID NO: 10) |

Example 5

Establishment of Real-time PCR Conditions

By following the real-time PCT procedure in Example 1 and using the probes described in Example 4, the parameters of primer concentration, probe concentration, PCR reaction temperature, and time were varied to discover the optimal conditions. Tables 12 and 13 show the selected conditions.

TABLE 12

| | Conc. | μL |
|---|---|---|
| Premix | 2× | 10 |
| ROX | 50× | 0.4 |
| Probe | 10 μM | 0.8 |
| Primer pair | 5 μM each | 0.8 |
| H$_2$O | | 4.0 |
| Total | | 16.0 |

TABLE 13

| Step | Temp. | Time | Cycle | Ramp time |
|---|---|---|---|---|
| 1 | 50° C. | 2 min | 1 | Auto |
| 2 | 95° C. | 10 min | 1 | Auto |
| 3 | 95° C. | 5 sec | 40 | Auto |
| | 60° C. | 30 sec | | Auto |
| 4 | 20° C. | 1 min | 1 | Auto |

Example 6

Verification of Universality in Wheat Varieties

A comparison of the detected amount was performed by real-time PCR using the TaqMan procedure for 40 varieties of wheat. The amplification product W×012 (SEQ ID NO: 31) amplified by the primers W×012-F and W×012-R was used as a comparative control. The PRP03-F and PRP03-R were used as the primers and PRPTaq-1 was used as the probe. The amplification product PRP03 (SEQ ID NO: 15) amplified by the primers PRP03-F and PRP03-R was detected in all 40 varieties. W×012 was detected in all varieties except durum wheat and waxy wheat varieties. In the comparison with PRP03, the W×012:PRP03 ratio was approximately 1:1 in all varieties wherein W×012 was detected.

Figure 5:
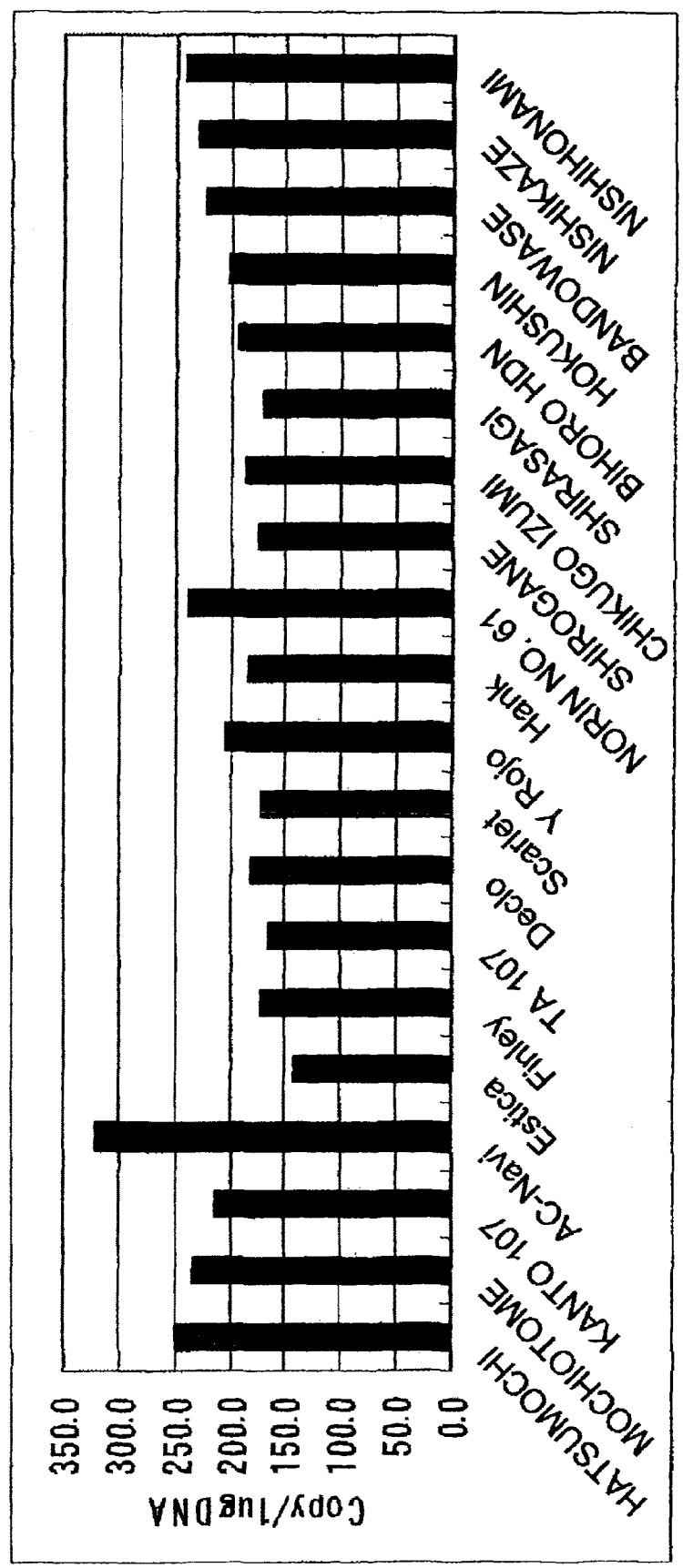
FIG. 5 shows the detection Examples in 20 of 40 varieties of wheat wherein PRP03 was detected.

FIG. 5 shows the detection examples of 20 of the 40 varieties of wheat wherein PRP03 was detected. In FIG. 5 the terms Hatsumochi and Mochiotome indicate varieties of waxy wheat, and AC-Navi refers to the AC Navigator variety of durum wheat. These were all detected.

Example 7

Estimation Test of Contamination Rate by Hypothetical GM Wheat

At the present time GM wheat is produced by Monsanto, etc., but it is very difficult to obtain. Therefore, a test was conducted using a hypothetical GM wheat to verify whether or not an estimation of the GM wheat contamination rate is possible by quantitation of the endogenous wheat gene discovered by the present invention.

Because the GM wheat produced by Monsanto is imparted with a Roundup® resistance gene, it was decided to use GM soybeans, which are a GMO imparted with the same Roundup® resistance gene. In other words, GM soybean seeds were pulverized, AC Barrie variety wheat seeds were pulverized and mixed therewith, and that was used as the hypothetical GM wheat. The mix ratio of both was investigated in preliminary tests so that the internal standard ratio would approach 1, and the mix ratio of GM soybeans to wheat was determined as 6:94. Quantitation of the Roundup® resistance gene and the endogenous gene (PRP region) was performed by real-time PCR with a TaqMan probe using DNA extracted from the hypothetical GM wheat as a template under the conditions shown in Example 5. (PRP-Taq2 was used as the probe, and the primers shown in Table 14 were used as primers. In the table, RRS refers to the Roundup® resistance gene.) The sequence amplified at that time is identified as SEQ ID NO: 32. The numerical value resulting when the obtained RRS quantitative value was divided by the endogenous wheat gene quantitative value was used as an internal standard ratio (1.0).

Figure 6:
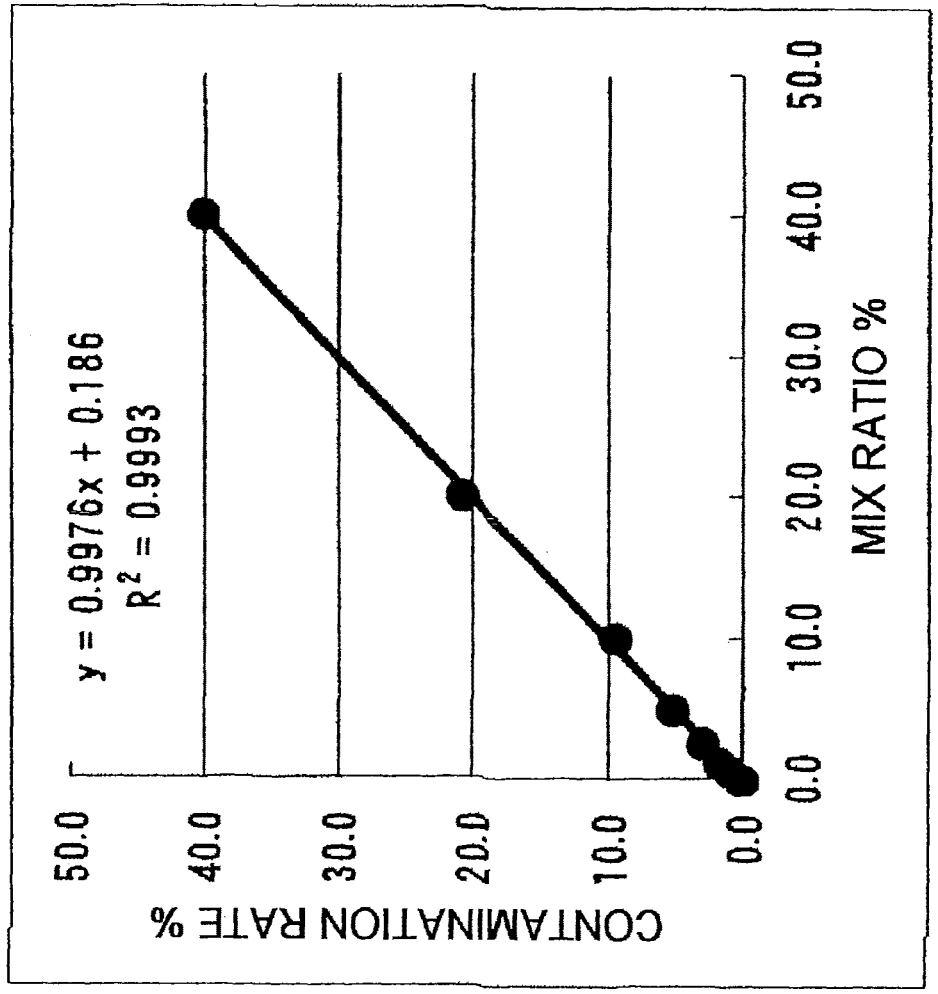
FIG. 6 shows the results when the hypothetical GM wheat contamination rate was determined using the results obtained when DNA was extracted from a sample wherein the hypothetical GM wheat was arbitrarily mixed with separately pulverized wheat (Yecora Rojo variety), and using this DNA as a template and following the method of the present invention, the endogenous wheat gene and Roundup® resistance gene were quantitated.

DNA was extracted from a sample obtained by arbitrarily mixing the hypothetical GM wheat with separately pulverized wheat (Yecora Rojo variety), and using this DNA as a template and following the method of the present invention, the endogenous wheat gene and Roundup® resistance gene were quantitated. FIG. 6 shows the hypothetical GM wheat contamination rate determined from those results. It was confirmed that the contamination rate determined by a calculation in accordance with the method of the present invention shows a high correlation with the actual mix ratio. More specifically the detected amount of GM wheat (copy number concentration: copy/µL) per volume of obtained template solution was divided by the detected amount (copy number concentration: copy/µL) per volume of obtained template solution of endogenous wheat gene. That quotient was divided by the internal standard ratio of 1.0 and multiplied by 100, and the resulting quotient was used as the GM contamination rate.

Example 8

Specificity Verification Test

A specificity test was performed to verify that the method according to the present invention does not have cross-reactivity with other crops. Barley, oats, rye, rice, sorghum, rapeseed, maize, buckwheat, and kibi millet were used as the other crops. DNA was extracted from these crops, and real-time PCR was performed using the DNA as a template under the conditions established in accordance with the method presented in Example 5.

Two types of primer pairs, PRP03-F and PRP03-R, and PRP03-F and PRP07-R were used, and PRP-Taq2 was used as the probe.

Figure 7:
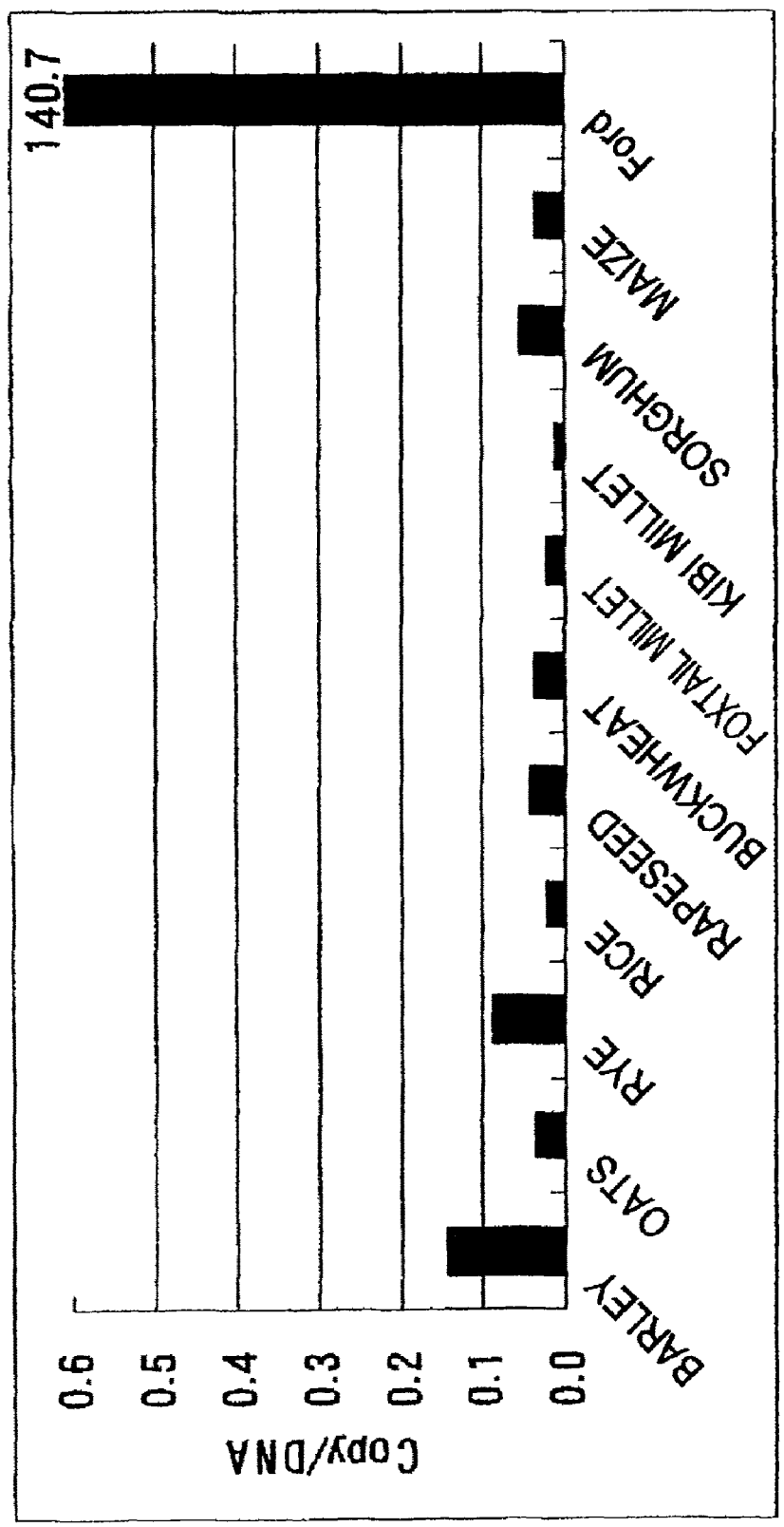
FIG. 7 shows the results of the verification test for cross-reactivity with other crops performed using two types of primer pairs, PRP03-F and PRP03-R, and PRP03-F and PRP07-R, and PRP-Taq2 as the probe.

FIG. 7 shows the results. When the primer pair of PRP03-F and PRP07-R was used, 140 copies per 1 µg of DNA were detected in wheat, but in the above crops no more than 0.2 copies were detected. In other words, the nonspecific detection rate in those crops was no more than 0.05%, and because this value is much lower than the standard error in wheat detection, it was confirmed that these crops do not affect the quantitation of the endogenous wheat gene. When the primer pair of RPR03-F and PRP03-R was used, although a detection of 0.3% with respect to wheat was found in barley, the rate was no more than 0.05% in other crops. Therefore, even when this primer pair was used, the value was much lower than the standard error in wheat detection, and it was confirmed that these crops do not affect the quantitation of the endogenous wheat gene.

TABLE 14

| Gene | Name | Sequence | Amplicon size (bp) |
|---|---|---|---|
| PRP | prp03-F | 5'-aag cca ccg atg act gac aat-3' (SEQ ID NO: 3) | 231 |
|  | prp07-R | 5'-cgc aaa tga taa tta cag aat agt agt ac-3' (SEQ ID NO: 4) |  |
| RRS | RRS2-F | 5'-cct tta gga ttt cag cat cag tgg-3' (SEQ ID NO: 33) | 121 |
|  | RRS2-R | 5'-gac ttg tcg ccg gga atg-3' (SEQ ID NO: 34) |  |

We claim:

1. A method of detecting or quantitating endogenous wheat DNA in a test sample by a polymerase chain reaction, the method comprising:
   providing a nucleic acid molecule in the test sample or a nucleic acid molecule extracted from the test sample as a template to amplify a region consisting of a nucleotide sequence identified as SEQ ID NO: 2 or a partial sequence thereof that is at least 80 nucleotide bases or more of SEQ ID NO: 2 with a primer pair capable of amplifying that region, and
   detecting or quantitating the amplified region as the endogenous wheat DNA.

2. The method according to claim 1, wherein the region consisting of the partial sequence of the nucleotide sequence identified as SEQ ID NO: 2 is a region consisting of any one of nucleotide sequences identified as SEQ ID NOS: 11 to 18.

3. The method according to claim 1, wherein the primer pair is a primer pair selected from a group consisting of:
(i) a primer pair consisting of a nucleic acid molecule comprising the nucleotide sequence identified as SEQ ID NO: 3 and a nucleic acid molecule comprising the nucleotide sequence identified as SEQ ID NO: 4;
(ii) a primer pair consisting of a nucleic acid molecule comprising the nucleotide sequence identified as SEQ ID NO: 5 and a nucleic acid molecule comprising the nucleotide sequence identified as SEQ ID NO: 4;
(iii) a primer pair consisting of a nucleic acid molecule comprising the nucleotide sequence identified as SEQ ID NO: 3 and a nucleic acid molecule comprising the nucleotide sequence identified as SEQ ID NO: 6;
(iv) a primer pair consisting of a nucleic acid molecule comprising the nucleotide sequence identified as SEQ ID NO: 5 and a nucleic acid molecule comprising the nucleotide sequence identified as SEQ ID NO: 6;
(v) a primer pair consisting of a nucleic acid molecule comprising the nucleotide sequence identified as SEQ ID NO: 3 and a nucleic acid molecule comprising the nucleotide sequence identified as SEQ ID NO: 7;
(vi) a primer pair consisting of a nucleic acid molecule comprising the nucleotide sequence identified as SEQ ID NO: 3 and a nucleic acid molecule comprising the nucleotide sequence identified as SEQ ID NO: 8;
(vii) a primer pair consisting of a nucleic acid molecule comprising the nucleotide sequence identified as SEQ ID NO: 5 and a nucleic acid molecule comprising the nucleotide sequence identified as SEQ ID NO: 8;
(viii) a primer pair consisting of a nucleic acid molecule comprising the nucleotide sequence identified as SEQ ID NO: 5 and a nucleic acid molecule comprising the nucleotide sequence identified as SEQ ID NO: 7; and
(ix) a primer pair consisting of a pair of nucleic acid molecules with each nucleic acid molecule comprising a nucleotide sequence in common with at least 80% continuous nucleotide sequence of each nucleic acid molecule in the primer pairs in (i) to (viii) above.

4. The method according to any one of claims 1 to 3, wherein each primer in the primer pair is a nucleic acid molecule having 15 to 40 bases long.

5. The method according to any one of claims 1 to 3, wherein the region amplified in the polymerase chain reaction is detected using a probe identified as SEQ ID NO: 9 or 10.

6. A method of determining a contamination rate of genetically modified wheat in a test sample, the method comprising:
preparing two or more types of concentration dilution series of solutions containing an endogenous wheat DNA and at least one type of a genetically modified wheat-specific DNA,
performing quantitative polymerase chain reactions for each,
amplifying the endogenous wheat DNA and at least one type of the genetically modified wheat-specific DNA,
determining a calibration curve for each partial region,
performing, for the test sample, a quantitative polymerase chain reaction under the same conditions as determining the calibration curves, and
determining the number of the endogenous wheat DNA molecules and the number of the genetically modified wheat-specific DNA molecules present in the test sample using the calibration curve,
wherein the endogenous wheat DNA consists of the nucleotide sequence identified as SEQ ID NO: 2 or a partial sequence thereof that is at least 80 nucleotide bases or more of SEQ ID NO: 2.

7. The method according to claim 6, further comprising determining the contamination rate of genetically modified wheat in the test sample by calculating a formula 100×A/B using:
a ratio A obtained by dividing the number of the genetically modified wheat-specific DNA molecules by the number of the endogenous wheat DNA molecules present in the test sample; and
a ratio B obtained by dividing the number of DNA molecules specific to each strain of genetically modified wheat determined by performing quantitative polymerase chain reactions using each strain of genetically modified wheat by the number of endogenous wheat DNA molecules.

8. The method according to claim 6, wherein amplification of the endogenous wheat DNA is performed using at least one primer pair selected from a group consisting of:
(i) a primer pair consisting of a nucleic acid molecule comprising the nucleotide sequence identified as SEQ ID NO: 3 and a nucleic acid molecule comprising the nucleotide sequence identified as SEQ ID NO: 4;
(ii) a primer pair consisting of a nucleic acid molecule comprising the nucleotide sequence identified as SEQ ID NO: 5 and a nucleic acid molecule comprising the nucleotide sequence identified as SEQ ID NO: 4;
(iii) a primer pair consisting of a nucleic acid molecule comprising the nucleotide sequence identified as SEQ ID NO: 3 and a nucleic acid molecule comprising the nucleotide sequence identified as SEQ ID NO: 6;
(iv) a primer pair consisting of a nucleic acid molecule comprising the nucleotide sequence identified as SEQ ID NO: 5 and a nucleic acid molecule comprising the nucleotide sequence identified as SEQ ID NO: 6;
(v) a primer pair consisting of a nucleic acid molecule comprising the nucleotide sequence identified as SEQ ID NO: 3 and a nucleic acid molecule comprising the nucleotide sequence identified as SEQ ID NO: 7;
(vi) a primer pair consisting of a nucleic acid molecule comprising the nucleotide sequence identified as SEQ ID NO: 3 and a nucleic acid molecule comprising the nucleotide sequence identified as SEQ ID NO: 8;
(vii) a primer pair consisting of a nucleic acid molecule comprising the nucleotide sequence identified as SEQ ID NO: 5 and a nucleic acid molecule comprising the nucleotide sequence identified as SEQ ID NO: 8;
(viii) a primer pair consisting of a nucleic acid molecule comprising the nucleotide sequence identified as SEQ ID NO: 5 and a nucleic acid molecule comprising the nucleotide sequence identified as SEQ ID NO: 7; and
(ix) a primer pair consisting of a pair of nucleic acid molecules with each nucleic acid molecule comprising a nucleotide sequence in common with at least 80% continuous nucleotide sequence of each nucleic acid molecule in the primer pairs in (i) to (viii) above.

9. A method of determining a contamination rate of genetically modified wheat in a test sample, the method comprising:
preparing two or more types of concentration dilution series of solutions containing an endogenous wheat DNA and at least one type of a genetically modified wheat-specific DNA,
performing quantitative polymerase chain reactions for each,
amplifying the endogenous wheat DNA and at least one type of the genetically modified wheat-specific DNA,
determining a calibration curve for each partial region, performing, for the test sample, a quantitative polymerase chain reaction under the same conditions as determining the calibration curves, and determining the number of the endogenous wheat DNA molecules and the number of the genetically modified wheat-specific DNA molecules present in the test sample using the calibration curve, wherein the endogenous wheat DNA consists of a nucleotide sequence having at least 80% homology with the DNA consisting of the nucleotide sequence identified as SEQ ID NO: 2 or a partial sequence thereof limitation—that is at least 80 nucleotide bases or more of SEQ ID NO: 2 and wherein the endogenous wheat DNA consist of a sequence capable of being amplified by the polymerase chain reaction using any of the primer pairs according to claim 3.

10. A method of determining a contamination rate of genetically modified wheat in a test sample, the method comprising:

preparing two or more types of concentration dilution series of solutions containing an endogenous wheat DNA and at least one type of a genetically modified wheat-specific DNA, performing quantitative polymerase chain reactions for each, amplifying the endogenous wheat DNA and at least one type of the genetically modified wheat-specific DNA, determining a calibration curve for each partial region, performing, for the test sample, a quantitative polymerase chain reaction under the same conditions as determining the calibration curves, and determining the number of the endogenous wheat DNA molecules and the number of the genetically modified wheat-specific DNA molecules present in the test sample using the calibration curve, wherein the endogenous wheat DNA consists of a sequence capable of being amplified by the polymerase chain reaction using any of the primer pairs according to claim 3.

* * * * *

UNITED STATES PATENT AND TRADEMARK OFFICE
CERTIFICATE OF CORRECTION

PATENT NO.         : 8,173,400 B2
APPLICATION NO.    : 12/300973
DATED              : May 8, 2012
INVENTOR(S)        : Shinjiro Imai et al.

It is certified that error appears in the above-identified patent and that said Letters Patent is hereby corrected as shown below:

In claim 9, column 39, line 12, after "sequence thereof" delete "limitation —".

Signed and Sealed this
Twenty-seventh Day of November, 2012

David J. Kappos
*Director of the United States Patent and Trademark Office*

SEQUENCE LISTING

<160> NUMBER OF SEQ ID NOS: 34

<210> SEQ ID NO 1
<211> LENGTH: 1487
<212> TYPE: DNA
<213> ORGANISM: Triticum aestivum
<220> FEATURE:
<221> NAME/KEY: misc_feature
<222> LOCATION: (2)..(122)
<223> OTHER INFORMATION: the region amplified by primers PRP01-F and
   PRP01-R
<220> FEATURE:
<221> NAME/KEY: misc_feature
<222> LOCATION: (1158)..(1487)
<223> OTHER INFORMATION: the region to be amplified for the method of
   the present invention

<400> SEQUENCE: 1

```
ggcgacaccc catccacttt atctcagttg agaggtttag aagcgcgcgg tgaagcacaa      60
agtgcagcaa gagctgcgag aaggagcgag cagcaatggc gaggcacagc ctccttgccg     120
tgctcctcgt cgggctggtc gcggcctccg gcttcagcca ggcggccgcc gctggccggg     180
gccttgctga gaagctcccc gagccggagc ccaagccgac gccgtaccca gagcccaagc     240
cgcaacccaa gccagagcca atgcctaagc ctgaacccat gccaaagcca gagcctaagc     300
ctctgcctaa acctgaaccc atgccaaaac cagagcctaa gcctctgccc aaacctgaac     360
ccatgccaaa gccagagccc aaaccggagc cgaagccgga gccgatccca aagcccgaac     420
caaagcctga gcccaagcct gacccgatgc ccaaacctga gcctaagcct gagcccaagc     480
cagagccgat gccaaaccg gaaccaaagc cagagcccaa gcccgagcct atgccaaaac     540
ctgaaccaaa gcccgagccc aaacccgagc cgatgaagcc tgagcctaag ccgatgccaa     600
aacccgaacc gaagccagag cccaagcccg agccgatgcc taaaccagaa ccaaagccag     660
agcccaaacc cgagccgata aagcctgagc ctaagccgat gccgaaaccc gaacctaagc     720
cagagcccaa gcctgagccg atgccaaaac cggaacccaa gcctgagccc aagcctgagc     780
cgatgccaaa accggagccc aagcccgagc caagcccga gccgatgcca aaaccggaac     840
caaagcctga gcccaagcct acccaatgc ccaaacctga gcctaagcct gagcccaaac     900
ccgagccgat gccaaaacca gaaccaaagc cagagcccaa acccgagccg atgccaaagc     960
cggaaccaaa gccagagccc aaacccgagc caagccaga gccgatgcca agccggaac    1020
caaagcccga gcccaagccc gagccaatgc gaagccaga accgaagcca gagcccaagc    1080
ctgagccgat gccaaagcca gagcctaagc ccaaaccatt gcctaaacca gagcctaagc    1140
ctgaacctat gcctaagcca gagcccaagc ctgagcccga accgaagccg agccgcctc    1200
cgaagggcaa gccaccgatg actgacaatt gatgtgatac tcacatatga cagctgaagg    1260
aggagatcga ccccgtccgg agccacgatg tgctatttct agaataagtg gcatagtatc    1320
cggttagcga gatagtgatg atgcatcttt ttgtattcct tgtattccac cattccttt     1380
agtttctgtt gttccatgca cccatgatga gtactactat tctgtaatta tcatttgcgt    1440
gttggtatat gttcatctgt gcacatgact cagttgttct ttcgtgt                 1487
```

<210> SEQ ID NO 2
<211> LENGTH: 330
<212> TYPE: DNA
<213> ORGANISM: Triticum aestivum
<220> FEATURE:
<221> NAME/KEY: misc_feature
<223> OTHER INFORMATION: the region to be amplified for the method of the present invention

<400> SEQUENCE: 2

```
ccagagccca agcctgagcc cgaaccgaag ccggagccgc ctccgaaggg caagccaccg    60
atgactgaca attgatgtga tactcacata tgacagctga aggaggagat cgaccccgtc   120
cggagccacg atgtgctatt tctagaataa gtggcatagt atccggttag cgagatagtg   180
atgatgcatc tttttgtatt ccttgtattc caccattcct tttagtttct gttgttccat   240
gcacccatga tgagtactac tattctgtaa ttatcatttg cgtgttggta tatgttcatc   300
tgtgcacatg actcagttgt tctttcgtgt                                    330
```

<210> SEQ ID NO 3
<211> LENGTH: 21
<212> TYPE: DNA
<213> ORGANISM: artificial
<220> FEATURE:
<223> OTHER INFORMATION: PCR primer PRP03-F

<400> SEQUENCE: 3

```
aagccaccga tgactgacaa t                                              21
```

<210> SEQ ID NO 4
<211> LENGTH: 29
<212> TYPE: DNA
<213> ORGANISM: artificial
<220> FEATURE:
<223> OTHER INFORMATION: PCR primer PRP07-R

<400> SEQUENCE: 4

```
cgcaaatgat aattacagaa tagtagtac                                      29
```

<210> SEQ ID NO 5
<211> LENGTH: 17
<212> TYPE: DNA
<213> ORGANISM: artificial
<220> FEATURE:
<223> OTHER INFORMATION: PRP primer PRP04-F

<400> SEQUENCE: 5

```
gcctccgaag ggcaagc                                                   17
```

<210> SEQ ID NO 6
<211> LENGTH: 23
<212> TYPE: DNA
<213> ORGANISM: artificial
<220> FEATURE:
<223> OTHER INFORMATION: PCR primer PRP06-R

<400> SEQUENCE: 6

```
gaacatatac caacacgcaa atg                                            23
```

<210> SEQ ID NO 7
<211> LENGTH: 21
<212> TYPE: DNA
<213> ORGANISM: artificial
<220> FEATURE:
<223> OTHER INFORMATION: PCR primer PRP03-R

<400> SEQUENCE: 7

```
cgctaaccgg atactatgcc a                                              21
```

<210> SEQ ID NO 8
<211> LENGTH: 20
<212> TYPE: DNA

```
<213> ORGANISM: artificial
<220> FEATURE:
<223> OTHER INFORMATION: PCR primer PRP04-R

<400> SEQUENCE: 8
atagcacatc gtggctccgg                                                    20

<210> SEQ ID NO 9
<211> LENGTH: 20
<212> TYPE: DNA
<213> ORGANISM: artificial
<220> FEATURE:
<223> OTHER INFORMATION: PCR probe PRP-Taq1

<400> SEQUENCE: 9
tcgaccccgt ccggagccac                                                    20

<210> SEQ ID NO 10
<211> LENGTH: 23
<212> TYPE: DNA
<213> ORGANISM: artificial
<220> FEATURE:
<223> OTHER INFORMATION: PCR probe PRP-Taq2

<400> SEQUENCE: 10
agctgaagga ggagatcgac ccc                                                23

<210> SEQ ID NO 11
<211> LENGTH: 231
<212> TYPE: DNA
<213> ORGANISM: Triticum aestivum
<220> FEATURE:
<221> NAME/KEY: misc_feature
<223> OTHER INFORMATION: the region amplified by primers PRP03-F and
      PRP07-R

<400> SEQUENCE: 11
aagccaccga tgactgacaa ttgatgtgat actcacatat gacagctgaa ggaggagatc         60
gaccccgtcc ggagccacga tgtgctattt ctagaataag tggcatagta tccggttagc        120
gagatagtga tgatgcatct ttttgtattc cttgtattcc accattcctt ttagtttctg        180
ttgttccatg cacccatgat gagtactact attctgtaat tatcatttgc g                 231

<210> SEQ ID NO 12
<211> LENGTH: 244
<212> TYPE: DNA
<213> ORGANISM: Triticum aestivum
<220> FEATURE:
<221> NAME/KEY: misc_feature
<223> OTHER INFORMATION: the region amplified by primers PRP04-F and
      PRP07-R

<400> SEQUENCE: 12
gcctccgaag ggcaagccac cgatgactga caattgatgt gatactcaca tatgacagct         60
gaaggaggag atcgaccccg tccggagcca cgatgtgcta tttctagaat aagtggcata        120
gtatccggtt agcgagatag tgatgatgca tcttttttgta ttccttgtat tccaccattc        180
cttttagttt ctgttgttcc atgcacccat gatgagtact actattctgt aattatcatt        240
tgcg                                                                    244

<210> SEQ ID NO 13
<211> LENGTH: 246
<212> TYPE: DNA
<213> ORGANISM: Triticum aestivum
<220> FEATURE:
```

<221> NAME/KEY: misc_feature
<223> OTHER INFORMATION: the region amplified by primers PRP03-F and
      PRP06-R

<400> SEQUENCE: 13
aagccaccga tgactgacaa ttgatgtgat actcacatat gacagctgaa ggaggagatc    60
gaccccgtcc ggagccacga tgtgctattt ctagaataag tggcatagta tccggttagc   120
gagatagtga tgatgcatct ttttgtattc cttgtattcc accattcctt ttagtttctg   180
ttgttccatg cacccatgat gagtactact attctgtaat tatcatttgc gtgttggtat   240
atgttc                                                              246

<210> SEQ ID NO 14
<211> LENGTH: 259
<212> TYPE: DNA
<213> ORGANISM: Triticum aestivum
<220> FEATURE:
<221> NAME/KEY: misc_feature
<223> OTHER INFORMATION: the region amplified by primers PRP04-F and
      PRP06-R

<400> SEQUENCE: 14
gcctccgaag ggcaagccac cgatgactga caattgatgt gatactcaca tatgacagct    60
gaaggaggag atcgaccccg tccggagcca cgatgtgcta tttctagaat aagtggcata   120
gtatccggtt agcgagatag tgatgatgca tcttttgta ttccttgtat tccaccattc   180
cttttagttt ctgttgttcc atgcacccat gatgagtact actattctgt aattatcatt   240
tgcgtgttgg tatatgttc                                                259

<210> SEQ ID NO 15
<211> LENGTH: 121
<212> TYPE: DNA
<213> ORGANISM: Triticum aestivum
<220> FEATURE:
<221> NAME/KEY: misc_feature
<223> OTHER INFORMATION: the region amplified by primers PRP03-F and
      PRP03-R

<400> SEQUENCE: 15
aagccaccga tgactgacaa ttgatgtgat actcacatat gacagctgaa ggaggagatc    60
gaccccgtcc ggagccacga tgtgctattt ctagaataag tggcatagta tccggttagc   120
g                                                                   121

<210> SEQ ID NO 16
<211> LENGTH: 88
<212> TYPE: DNA
<213> ORGANISM: Triticum aestivum
<220> FEATURE:
<221> NAME/KEY: misc_feature
<223> OTHER INFORMATION: the region amplified by primers PRP03-F and
      PRP04-R

<400> SEQUENCE: 16
aagccaccga tgactgacaa ttgatgtgat actcacatat gacagctgaa ggaggagatc    60
gaccccgtcc ggagccacga tgtgctat                                       88

<210> SEQ ID NO 17
<211> LENGTH: 101
<212> TYPE: DNA
<213> ORGANISM: Triticum aestivum
<220> FEATURE:
<221> NAME/KEY: misc_feature
<223> OTHER INFORMATION: the region amplified by primers PRP04-F and

PRP04-R

<400> SEQUENCE: 17
gcctccgaag ggcaagccac cgatgactga caattgatgt gatactcaca tatgacagct    60
gaaggaggag atcgaccccg tccggagcca cgatgtgcta t    101

<210> SEQ ID NO 18
<211> LENGTH: 134
<212> TYPE: DNA
<213> ORGANISM: Triticum aestivum
<220> FEATURE:
<221> NAME/KEY: misc_feature
<223> OTHER INFORMATION: the region amplified by primers PRP04-F and
      PRP03-R

<400> SEQUENCE: 18
gcctccgaag ggcaagccac cgatgactga caattgatgt gatactcaca tatgacagct    60
gaaggaggag atcgaccccg tccggagcca cgatgtgcta tttctagaat aagtggcata   120
gtatccggtt agcg    134

<210> SEQ ID NO 19
<211> LENGTH: 20
<212> TYPE: DNA
<213> ORGANISM: artificial
<220> FEATURE:
<223> OTHER INFORMATION: PCR primer PRP01-F

<400> SEQUENCE: 19
gcgacacccc atccacttta    20

<210> SEQ ID NO 20
<211> LENGTH: 18
<212> TYPE: DNA
<213> ORGANISM: artificial
<220> FEATURE:
<223> OTHER INFORMATION: PCR primer PRP01-R

<400> SEQUENCE: 20
cacggcaagg aggctgtg    18

<210> SEQ ID NO 21
<211> LENGTH: 20
<212> TYPE: DNA
<213> ORGANISM: artificial
<220> FEATURE:
<223> OTHER INFORMATION: PCR primer Wx012-F

<400> SEQUENCE: 21
ggtcgcagga acagaggtgt    20

<210> SEQ ID NO 22
<211> LENGTH: 19
<212> TYPE: DNA
<213> ORGANISM: artificial
<220> FEATURE:
<223> OTHER INFORMATION: PCR primer Wx012-R

<400> SEQUENCE: 22
ggtgttcctc cattgcgaa    19

<210> SEQ ID NO 23
<211> LENGTH: 23
<212> TYPE: DNA
<213> ORGANISM: artificial
<220> FEATURE:

<223> OTHER INFORMATION: PCR primer RRS-F

<400> SEQUENCE: 23
tggaaaagga aggtggctcc tac                    23

<210> SEQ ID NO 24
<211> LENGTH: 21
<212> TYPE: DNA
<213> ORGANISM: artificial
<220> FEATURE:
<223> OTHER INFORMATION: PCR primer RRS-R

<400> SEQUENCE: 24
gggaattgga tccggtaccg a                      21

<210> SEQ ID NO 25
<211> LENGTH: 30
<212> TYPE: DNA
<213> ORGANISM: artificial
<220> FEATURE:
<223> OTHER INFORMATION: PCR primer RRS-Sac-F

<400> SEQUENCE: 25
agagctctgg aaaaggaagg tggctcctac              30

<210> SEQ ID NO 26
<211> LENGTH: 21
<212> TYPE: DNA
<213> ORGANISM: artificial
<220> FEATURE:
<223> OTHER INFORMATION: PCR primer RRS-Sac-R

<400> SEQUENCE: 26
gggaattgga tccggtaccg a                      21

<210> SEQ ID NO 27
<211> LENGTH: 20
<212> TYPE: DNA
<213> ORGANISM: artificial
<220> FEATURE:
<223> OTHER INFORMATION: PCR primer Wx-F

<400> SEQUENCE: 27
ttttgttgtg ccgcttgcct                        20

<210> SEQ ID NO 28
<211> LENGTH: 22
<212> TYPE: DNA
<213> ORGANISM: artificial
<220> FEATURE:
<223> OTHER INFORMATION: PCR primer Wx-R

<400> SEQUENCE: 28
agtttagcgc gtcacagact ca                     22

<210> SEQ ID NO 29
<211> LENGTH: 28
<212> TYPE: DNA
<213> ORGANISM: artificial
<220> FEATURE:
<223> OTHER INFORMATION: PCR primer Wx-Xba-F

<400> SEQUENCE: 29
tctctagatt ttgttgtgcc gcttgcct               28

<210> SEQ ID NO 30

```
<211> LENGTH: 29
<212> TYPE: DNA
<213> ORGANISM: artificial
<220> FEATURE:
<223> OTHER INFORMATION: PCR primer Wx-Xba-R

<400> SEQUENCE: 30
tctctagagt ttagcgcgtc acagactca                                      29

<210> SEQ ID NO 31
<211> LENGTH: 102
<212> TYPE: DNA
<213> ORGANISM: Triticum aestivum
<220> FEATURE:
<221> NAME/KEY: misc_feature
<223> OTHER INFORMATION: the region amplified by primers Wx012-F and
      Wx012-R

<400> SEQUENCE: 31
ggtcgcggga acagaggtgt tcaaggcggc cgaaataggt tgccgcctgc ggcggaatcg    60
ccacccaccg tgaagttcac cgtttcgcaa tggaggaaca cc                       102

<210> SEQ ID NO 32
<211> LENGTH: 121
<212> TYPE: DNA
<213> ORGANISM: artificial
<220> FEATURE:
<223> OTHER INFORMATION: the region amplified by primers RRS-F and
      RRS-R; specific sequence of roundup resistant gene

<400> SEQUENCE: 32
cctttaggat ttcagcatca gtggctacag cctgcatgct tcacggtgca agcagccggc    60
ccgcaaccgc ccgcaaatcc tctggccttt ccggaaccgt ccgcattccc ggcgacaagt   120
c                                                                   121

<210> SEQ ID NO 33
<211> LENGTH: 24
<212> TYPE: DNA
<213> ORGANISM: Artificial
<220> FEATURE:
<223> OTHER INFORMATION: PCR primer RRS2-F

<400> SEQUENCE: 33
cctttaggat ttcagcatca gtgg                                           24

<210> SEQ ID NO 34
<211> LENGTH: 18
<212> TYPE: DNA
<213> ORGANISM: Artificial
<220> FEATURE:
<223> OTHER INFORMATION: PCR primer RRS2-R

<400> SEQUENCE: 34
gacttgtcgc cgggaatg                                                  18
```